United States Patent
Barry et al.

(10) Patent No.: US 8,449,549 B2
(45) Date of Patent: May 28, 2013

(54) ROD COERCER

(75) Inventors: David Barry, Teaneck, NJ (US); Rui Ferreira, Livingston, NJ (US)

(73) Assignee: EBI, LLC, Parsippany, NJ (US)

( * ) Notice: Subject to any disclaimer, the term of this patent is extended or adjusted under 35 U.S.C. 154(b) by 0 days.

(21) Appl. No.: 13/413,318

(22) Filed: Mar. 6, 2012

(65) Prior Publication Data

US 2012/0197318 A1  Aug. 2, 2012

Related U.S. Application Data

(63) Continuation of application No. 12/692,212, filed on Jan. 22, 2010, now Pat. No. 8,137,357, which is a continuation-in-part of application No. 12/357,782, filed on Jan. 22, 2009, now Pat. No. 8,128,629.

(51) Int. Cl.
    *A61B 17/70* (2006.01)

(52) U.S. Cl.
    USPC ............................ 606/86 A; 606/99; 606/205

(58) Field of Classification Search
    USPC .................... 606/86 A, 96, 99, 104, 205–209
    See application file for complete search history.

(56) References Cited

U.S. PATENT DOCUMENTS

| | | |
|---|---|---|
| 620,853 A | 3/1899 | Richter |
| 2,977,150 A | 3/1961 | Thomas |
| 4,411,259 A | 10/1983 | Drummond |
| 4,567,884 A | 2/1986 | Edwards |
| 4,863,439 A | 9/1989 | Sanderson |
| 5,020,519 A | 6/1991 | Hayes et al. |
| 5,195,541 A | 3/1993 | Obenchain |
| 5,364,397 A | 11/1994 | Hayes et al. |
| 5,591,165 A | 1/1997 | Jackson |
| 5,616,143 A | 4/1997 | Schlapfer et al. |
| 5,720,751 A | 2/1998 | Jackson |
| 5,810,878 A | 9/1998 | Burel et al. |
| 5,910,141 A | 6/1999 | Morrison et al. |
| 5,944,720 A | 8/1999 | Lipton |
| 5,951,564 A | 9/1999 | Schroder et al. |
| 6,036,692 A | 3/2000 | Burel et al. |
| 6,066,143 A | 5/2000 | Lane |
| 6,183,472 B1 | 2/2001 | Lutz |

(Continued)

FOREIGN PATENT DOCUMENTS

| | | |
|---|---|---|
| DE | 3203451 A1 | 12/1982 |
| DE | 3412769 A1 | 10/1985 |

(Continued)

OTHER PUBLICATIONS

"Surgical Technique," Moss Miami 3-Dimensional Spinal Instrumentation, Deputy Motech, Inc. (1995) (13 pages).

(Continued)

*Primary Examiner* — Eduardo C Robert
*Assistant Examiner* — Christina Negrelli Rodriguez
(74) *Attorney, Agent, or Firm* — McCarter & English, LLP

(57) ABSTRACT

A rod coercer for use in spinal fixation procedures is provided. In one embodiment, the rod coercer includes a handle having at least one rod contacting arm extending therefrom; an implant gripping assembly pivotally interconnected with the handle; and first and second implant gripping levers interconnected with the implant gripping assembly and including first and second protrusions biased to engage corresponding recesses of the implant. The protrusions can be selectively retracted from the recesses of the implant by pivoting the implant gripping levers.

10 Claims, 26 Drawing Sheets

U.S. PATENT DOCUMENTS

| | | |
|---|---|---|
| 6,440,133 B1 | 8/2002 | Beale et al. |
| 6,660,006 B2 | 12/2003 | Markworth et al. |
| 6,726,692 B2 | 4/2004 | Bette |
| 6,743,231 B1 | 6/2004 | Gray et al. |
| 6,746,449 B2 | 6/2004 | Jones et al. |
| 6,790,209 B2 | 9/2004 | Beale et al. |
| 7,090,679 B2 | 8/2006 | Saint-Martin et al. |
| 7,169,153 B2 | 1/2007 | Keller |
| 7,371,239 B2 | 5/2008 | Dec et al. |
| 7,608,078 B2 | 10/2009 | Berry |
| 8,128,629 B2 | 3/2012 | Barry et al. |
| 8,137,357 B2 | 3/2012 | Barry et al. |
| 2003/0225408 A1 | 12/2003 | Nichols et al. |
| 2004/0049191 A1 | 3/2004 | Markworth et al. |
| 2004/0106927 A1 | 6/2004 | Ruffner et al. |
| 2004/0147936 A1 | 7/2004 | Rosenberg et al. |
| 2004/0267275 A1 | 12/2004 | Cournoyer et al. |
| 2005/0059969 A1 | 3/2005 | McKinley |
| 2005/0149053 A1 | 7/2005 | Varieur et al. |
| 2005/0171540 A1 | 8/2005 | Lim et al. |
| 2005/0261702 A1 | 11/2005 | Oribe et al. |
| 2006/0009775 A1 | 1/2006 | Dec et al. |
| 2006/0036260 A1 | 2/2006 | Runco et al. |
| 2006/0074418 A1 | 4/2006 | Jackson |
| 2006/0166534 A1 | 7/2006 | Brumfield et al. |
| 2006/0166535 A1 | 7/2006 | Brumfield et al. |
| 2007/0276379 A1 | 11/2007 | Miller et al. |
| 2007/0282337 A1 | 12/2007 | Garamszegi |
| 2008/0045950 A1 | 2/2008 | Dewey |
| 2008/0234765 A1 * | 9/2008 | Frasier et al. ............... 606/86 A |

FOREIGN PATENT DOCUMENTS

| | | |
|---|---|---|
| DE | 4238339 A1 | 5/1994 |
| EP | 0608592 B1 | 8/1998 |
| FR | 2580166 A1 | 10/1986 |

OTHER PUBLICATIONS

Glazer, et al., "EBI Array Spinal Spinal System—Surgical Technique," (2005) (32 pages).

International Search Report of the International Searching Authority mailed Mar. 18, 2010, issued in connection with International Patent Appln. No. PCT/US10/21776 (4 pages).

Written Opinion of the International Searching Authority mailed Mar. 18, 2010, issued in connection with International Patent Appln. No. PCT/US10/21776 (8 pages).

Office Action dated Jun. 30, 2011, issued in connection with U.S. Appl. No. 12/692,212 now U.S. Patent No. 8,137,357 (11 pages).

Office Action dated Jul. 5, 2011, issued in connection with U.S. Appl. No. 12/357,782 now U.S. Patent No. 8,128,629 (9 pages).

Notice of Allowance dated Nov. 2, 2011, issued in connection with U.S. Appl. No. 12/357,782 now U.S. Patent No. 8,128,629 (5 pages).

Notice of Allowance dated Nov. 9, 2011, issued in connection with U.S. Appl. No. 12/692,212, now U.S. Patent No. 8,137,357 (10 pages).

* cited by examiner

ROD COERCER

RELATED APPLICATIONS

This application is a continuation of U.S. patent application Ser. No. 12/692,212 filed Jan. 22, 2010 now U.S. Pat. No. 8,137,357, which is a continuation-in-part of U.S. patent application Ser. No. 12/357,782 filed Jan. 22, 2009, now U.S. Pat. No. 8,128,629, the entire disclosures of which are both expressly incorporated herein by reference.

BACKGROUND OF THE INVENTION

1. Field of the Invention

The present invention relates to instruments for use in surgical applications, and more specifically, to a rod coercer for positioning a rod into a surgical implant during a spinal fixation procedure.

2. Related Art

In spinal fixation surgery, a rod and a set of vertebral implants (e.g., pedicle screws) are often used to correct spinal deformities. In such procedures, the rod is often bent to a desired shape using an appropriate rod bender. Then, a surgeon installs the implants in selected vertebral bodies along the length of the spine. Each implant usually includes a head which is shaped to receive a portion of the rod. After the implants have been installed, the rod is seated or "reduced" into the head of an implant, using a device which applies force to the rod and the implant, so that the implant and its associated vertebral body, and the rod, are drawn together, and a portion of the rod is seated in the head of the implant. Once the rod has been reduced into the head of the implant, a cap is engaged with (e.g., threaded into) the head of the implant and tightened to retain the rod in the head of the implant. This process may be repeated for each of the remaining implants, as needed, until the rod has been reduced into all of the implants. Once the procedure is complete, the spine conforms to the shape of the rod, to correct the spinal deformity. Thus, it is very important in such procedures to properly reduce a spinal rod into its associated implants.

Various devices for reducing a rod into an implant are known. One example is a simple forceps-type apparatus which includes articulating forceps branches and a bifurcated gripping nose which pivotally grips the head of an implant. When the forceps branches are closed and the pivotal grip is established, the device can be pivoted with respect to the implant to contact a rod and to exert force on same using a fulcrum arrangement, so as to reduce the rod into the head of the implant. Other devices include rod reducers having axially-aligned, concentric sleeves that move axially with respect to each other. Such devices include a pistol and trigger grip, as well as a ratchet mechanism interconnected with the trigger to urge one of the sleeves axially relative to another sleeve, causing prongs of the inner sleeve to grip an implant and the outer sleeve to reduce the rod into the implant. Another device includes a forceps-type instrument which grips an implant, and a separate articulating device which attaches to the forceps-type instrument and which pivots to reduce a rod into the implant.

SUMMARY OF THE INVENTION

The present invention relates to a rod coercer for use in spinal fixation procedures. The rod coercer includes first and second articulating forceps branches, first and second rod contacting arms extending from the first and second forceps branches, and first and second implant gripping arms pivotally interconnected with the first and second forceps branches. The forceps branches can be pivoted away from each other to open the implant gripping arms so that the arms can be positioned about the head of an implant and a rod to be reduced into the implant. The forceps branches can then be pivoted toward each other to clamp the implant gripping arms against the head of the implant, such that the head of the implant is fixedly gripped by the implant gripping arms. Optionally, corresponding locking tabs could be provided on the forceps branches for retaining the forceps branches and the implant gripping arms in a closed and locked position. After clamping the implant with the implant gripping arms, the forceps branches can be pivoted about the implant gripping arms so that the rod contacting arms contact the rod and the implant gripping arms draw the implant and the rod toward each other to reduce the rod into the head of the implant.

In another embodiment of the present invention, the rod coercer includes pivotally interconnected forceps branches, each of which is divided into upper and lower branch portions which are pivotally interconnected with each other so that the upper branch portion can be pivoted with respect to the lower branch portion. First and second implant gripping arms extend from the lower branch portions of the forceps branches. A rod contacting arm is provided, and is interconnected to an upper branch portion of one of the forceps branches by an upper linkage, and to a lower branch portion of the same forceps branch by a lower linkage. The forceps branches can be pivoted away from each other to open the implant gripping arms so that the arms can be positioned about the head of an implant and a rod to be reduced into the implant. The forceps branches can then be pivoted toward each other to clamp the implant gripping arms against the head of the implant, such that the head of the implant is fixedly engaged by the implant gripping arms. Optionally, corresponding locking tabs could be provided on the forceps branches for retaining the forceps branches and the implant gripping arms in a closed and locked position. After clamping the implant with the implant gripping arms, the upper branch portions can be pivoted with respect to the lower branch portions, so that the rod contacting arm contacts a rod and the implant gripping arms draw the implant and the rod together to reduce the rod into the head of the implant.

In another embodiment of the present invention, the forceps branches include first and second implant gripping arms which are pivotally interconnected with the branches, and a rod contacting arm coupled by gears to one of the forceps branches. An end of one of the forceps branches is attached to the face of a forceps gear, and an end of the rod contacting arm is attached to the face of an arm gear, such that the arm gear meshes with the forceps gear. The forceps branches can be pivoted away from each other to open the implant gripping arms so that the arms can be positioned about the head of an implant and a rod to be reduced into the implant. The forceps branches can then be pivoted toward each other to clamp the implant gripping arms against the head of the implant, such that the head of the implant is fixedly gripped by the implant gripping arms. Optionally, corresponding locking tabs could be provided on the forceps branches for retaining the forceps branches and the implant gripping arms in a closed and locked position. After clamping the implant with the implant gripping arms, the forceps branches can be pivoted with respect to the implant gripping arms, so that the forceps gear rotates the arm gear to pivot the rod contacting arm downwardly to contact the rod and the implant gripping arms draw the implant toward the rod to reduce the rod into the head of the implant.

In another embodiment of the present invention, the rod coercer includes first and second articulating handle branches, first and second rod contacting arms extending from the first and second handle branches, and first and second implant gripping arms pivotally interconnected with the first and second handle branches. The handle branches can be pivoted away from each other to open the implant gripping arms so that the arms can be positioned about the head of an implant and a rod to be reduced into the implant. The handle branches can then be pivoted toward each other to clamp the implant gripping arms against the head of the implant, such that the head of the implant is fixedly gripped by the implant gripping arms. Means for releasably locking the handle branches are provided for retaining the handle branches and the implant gripping arms in a closed and locked position. The means for releasably locking could include a ratcheting assembly having a hinged, toothed lever extending from one handle branch to engage an angled pawl on the second handle branch. After clamping the implant with the implant gripping arms, the handle branches can be pivoted about the implant gripping arms so that the rod contacting arms contact the rod and the implant gripping arms draw the implant and the rod toward each other to reduce the rod into the head of the implant.

In another embodiment of the present invention, the rod coercer includes a single handle having first and second implant gripping arms connected by a bridge and pivotally attached to the handle. Each implant gripping arm includes a spring-loaded locking lever for gripping sides of an implant. Springs bias protrusions on ends of the locking levers so that the protrusions extend through apertures in the implant gripping arms and into corresponding recesses in the implant to fixedly engage the implant. The levers can be pressed inward to disengage the protrusions from the recesses of the implant, to allow for removal of the rod coercer from the implant. Optionally, the levers can be L-shaped. After fixedly engaging the implant with the spring-loaded locking mechanism and implant gripping arms, the handle can be pivoted with respect to the implant gripping arms, so that the rod contacting arm contacts a rod and the implant gripping arms draw the implant and the rod together to reduce the rod into the head of the implant.

In another embodiment of the present invention, the rod coercer includes an adjustable rod contacting arm which can be adjusted to a desired angle with respect to the handles of the coercer. An implant gripping arm assembly (e.g., two implant gripping arms) is provided at ends of the handles, is pivotally connected thereto, and is positionable about the head of an implant and secured thereto. The rod contacting arm can then by adjusted to the desired angle using an adjustment assembly associated with the rod contacting arm. The adjustment assembly could include a screw, or threaded shaft, pivotally attached at one end to the handle and extending through a threaded aperture of the rod contacting arm. The adjustment assembly could also include a partial gear attached to the handle and in mechanical communication with a worm gear positioned within the rod contacting arm. Rotation of the worm gear, by a key or other device, alters the angle of the rod contacting arm. When the rod contacting arm is positioned at a desired angle, the handles can then be pivoted with respect to the implant gripping arms, so that the handle pivots the rod contacting arm downwardly to contact the rod and the implant gripping arms draw the implant toward the rod to reduce the rod into the head of the implant.

In another embodiment of the present invention, the rod coercer includes pivotally interconnected handle branches, each of which is divided into upper and lower branch portions which are pivotally interconnected with each other so that the upper branch potion can be pivoted with respect to the lower branch portion, an implant gripping assembly extending from the lower branch portions of the handle branches, and a rod contacting arm slidably and pivotally coupled to the upper branch portion by a first joint and slidably coupled to the lower branch by a second joint. The handle branches can be pivoted away from each other to open the implant griping arms so that the arms can be positioned about the head of an implant and a rod to be reduced into the implant. The handle branches can then be pivoted toward each other to clamp the implant gripping arms of the implant gripping assembly against the head of the implant, such that the head of the implant is fixedly engaged by the implant gripping arms. After engaging the implant with the implant gripping assembly, the upper branch portions can be pivoted with respect to the lower branch portions, causing the rod contacting arm to contact a rod and the implant gripping arms to draw the implant and the rod together to reduce the rod into the head of the implant.

In another embodiment of the present invention, the implant gripping arms of the rod coercer of the present invention are secured to each other by a flexible retainer. Pivoting the arms towards each other causes the flexible retainer to flex upwardly so that the implant may be gripped properly without interference from arch. Urging the gripping arms away from each other causes the retainer to flex.

BRIEF DESCRIPTION OF THE DRAWINGS

The foregoing features of the invention will be apparent from the following Detailed Description of the Invention, taken in connection with the accompanying drawings, in which.

DETAILED DESCRIPTION OF THE INVENTION

The present invention relates to a rod coercer for use in spinal fixation procedures. The rod coercer includes handle branches which can be pivoted along a first arc (i.e., about a first axis) to fixedly grip the head of an implant, and which can be pivoted along a second arc (i.e., about a second axis) to reduce a rod into the head of the implant. By the terms "coerce" and "reduce," it is meant the seating of a rod into a surgical implant through a mechanical application of force, such that the implant and the rod are drawn together and the rod is seated into the head of the implant.

Figure 1:
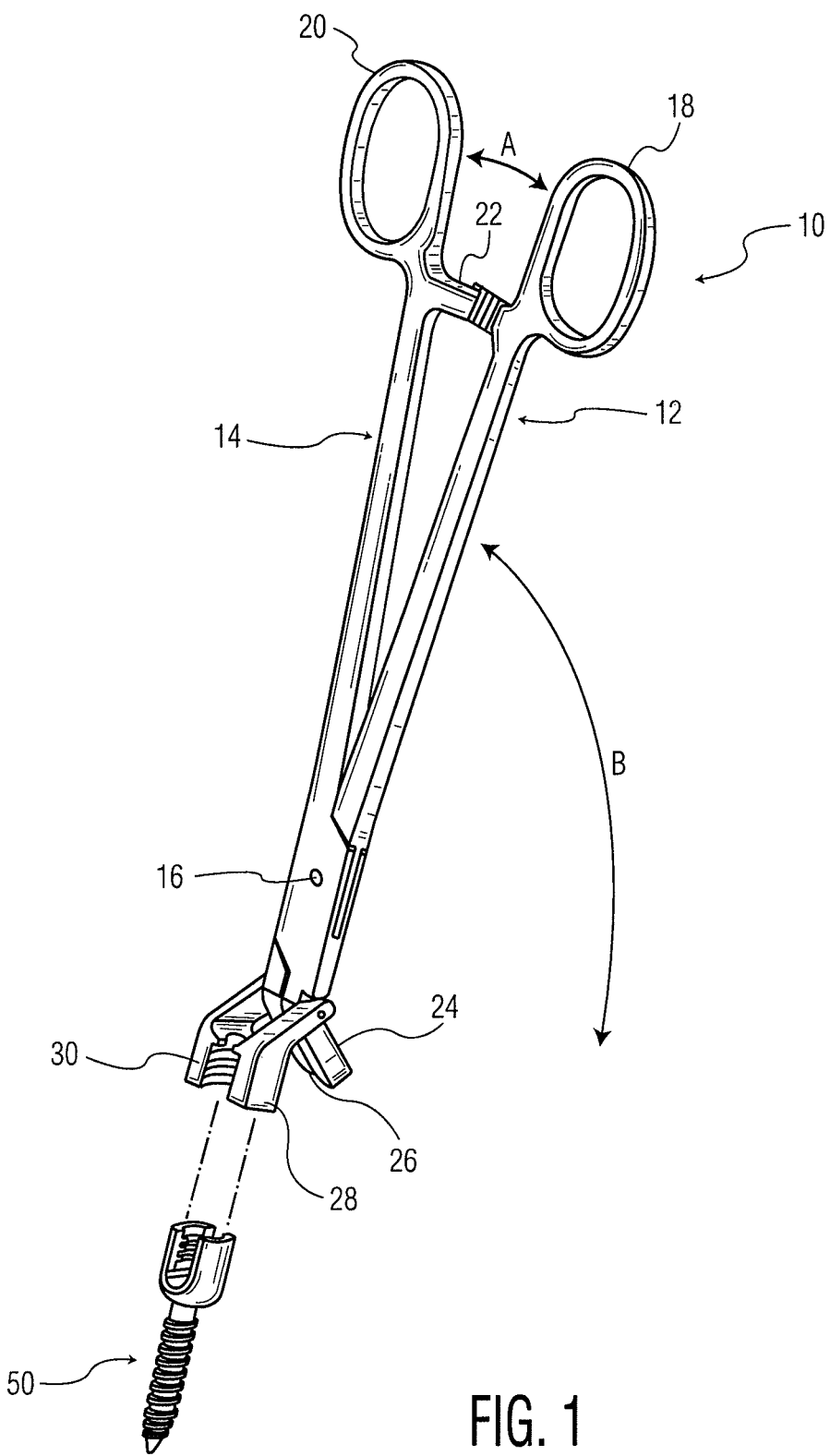
FIG. 1 is a perspective view showing the rod coercer of the present invention.

FIG. 1 is a perspective view showing the rod coercer 10 of the present invention. The rod coercer 10 includes right and left forceps branches 12, 14 which are pivotally interconnected at a pivot point 16 (e.g., by a pin extending through and pivotally interconnecting the branches 12, 14, or any other suitable type of pivotable interconnection). The branches 12, 14 include finger loops 18, 20 for receiving an operator's fingers. Optionally, corresponding locking tabs 22 (which included mating inner surfaces having teeth) could be provided for maintaining the branches 12, 14 in a closed and locked arrangement. Rod contacting arms 24, 26, which contact a rod to reduce it into an implant, are provided at the ends of the branches 12, 14. Implant gripping arms 28, 30 are pivotally interconnected with the branches 12, 14. The implant gripping arms 28, 30 fixedly grip an implant 50 (which could be a screw (e.g., pedicle screw), hook, or any other suitable implant which is configured to receive a rod), while the arms 24, 26 pivot with respect to the arms 28, 30 to reduce a rod into the implant 50.

To grip the implant 50, the forceps branches 12, 14 are pivoted away from each other about a first axis (in the direction shown by arrow A), which causes both the implant gripping arm 28 to move away from the implant gripping arm 30, and consequently, the arms 24, 26 similarly move away from each other. The arms 28, 30 are then positioned about opposite sides of the implant 50, as well as about a rod (not shown in FIG. 1) to be reduced into the implant 50. The forceps branches 12, 14 are then urged toward each other in the direction shown by arrow A, by an operator's fingers applying force to the branches 12, 14, so that the arms 28, 30 fixedly clamp the implant 50 and, consequently, the arms 24, 26 are brought together. The arms 28, 30 each have inner surfaces which could be cylindrical in shape or could have any other shape configured to match the shape of the implant 50. The inner surfaces contact the sides of the implant 50 and are held in a fixed position against the implant 50 when the arms 28, 30 are clamped against the implant 50. The locking tabs 22, if provided, maintains the forceps branches 12, 14 and the arms 28, 30 in a locked configuration, such that the arms 28, 30 remain clamped against the implant 50 when the operator releases his or her grip on the rod coercer 10. Advantageously, this frees the surgeon's hand to perform other tasks (if desired or necessary) prior to reduction of a rod, as discussed below. When the arms 28, 30 are clamped against the implant 50, the forceps branches 12, 14 can pivot with respect to the arms 28, 30, in the direction shown by arrow B. As discussed below, this motion allows for reduction of a rod into the implant 50. Thus, the rod coercer 10 can be pivoted in a first direction (i.e., about a first axis) to fixedly grip the implant 50, and can be pivoted in a second direction (i.e., about a second axis) generally transverse to the first direction to reduce a rod into the implant 50.

Figure 2:
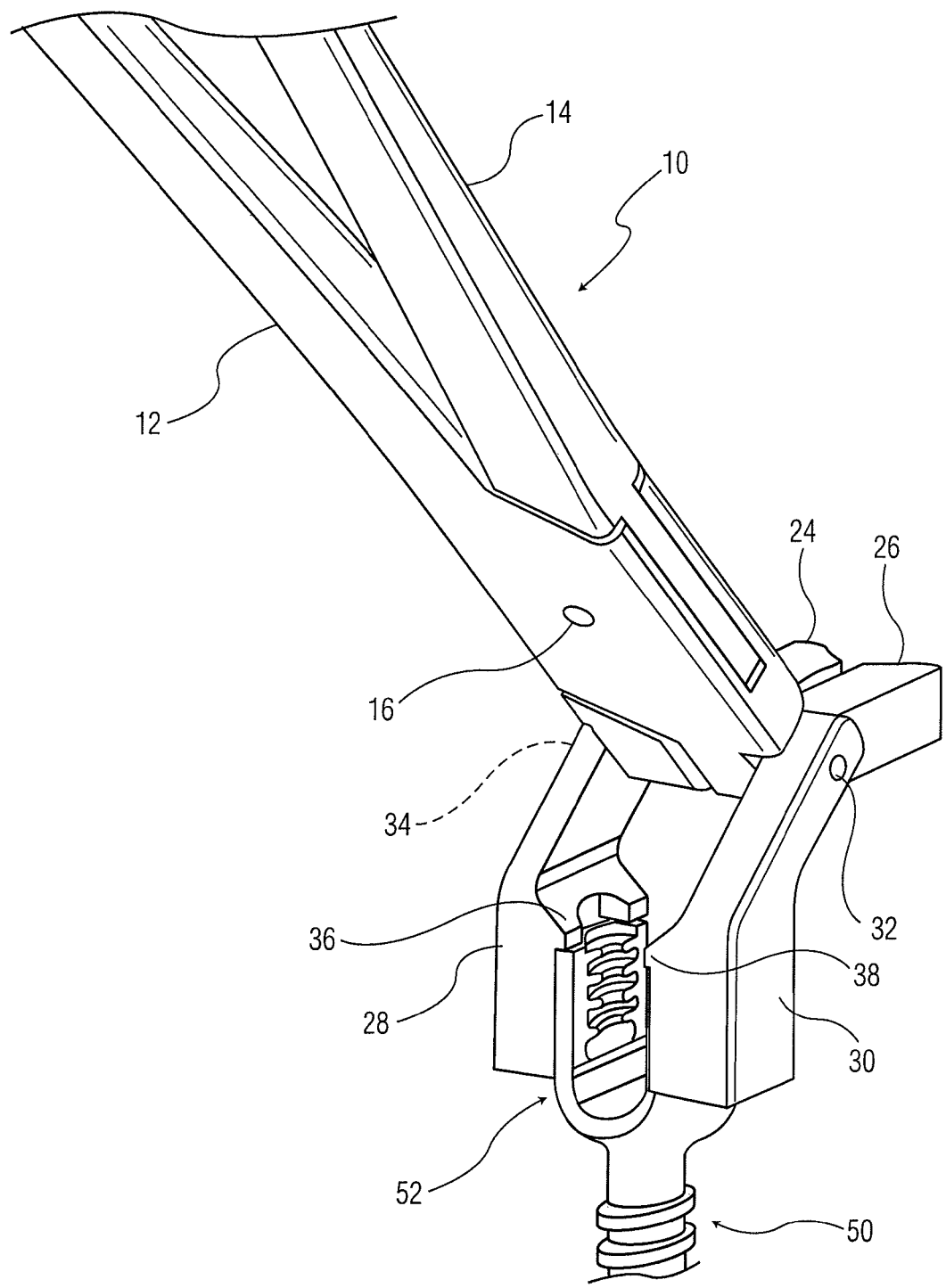
FIG. 2 is a partial perspective view showing the rod coercer of FIG. 1 in greater detail.

FIG. 2 is a partial perspective view showing the rod coercer 10 in greater detail. As mentioned above, the arms 28, 30 are pivotally interconnected with the branches 12, 14. Such a pivotable interconnection could be provided by a first pin 32 inserted through the arm 30 and the branch 12, and a second pin 34 inserted through the arm 28 and the branch 14, as well as any other suitable type of pivotable interconnection between the arms 28, 30 and the branches 12, 14, such as screws having smooth (pin-like) portions on the shafts thereof about which the arms 28, 30 rotate. The arms 28, 30 clamp opposite sides of the head 52 of the implant 50, and optionally include shoulders 36, 38. The space between the arms 28, 30 allows for insertion of a threaded cap, which could be threaded into the head 52 of the implant 50 to lock a rod to the implant 50, as well as an instrument for tightening such a cap.

Figure 3:
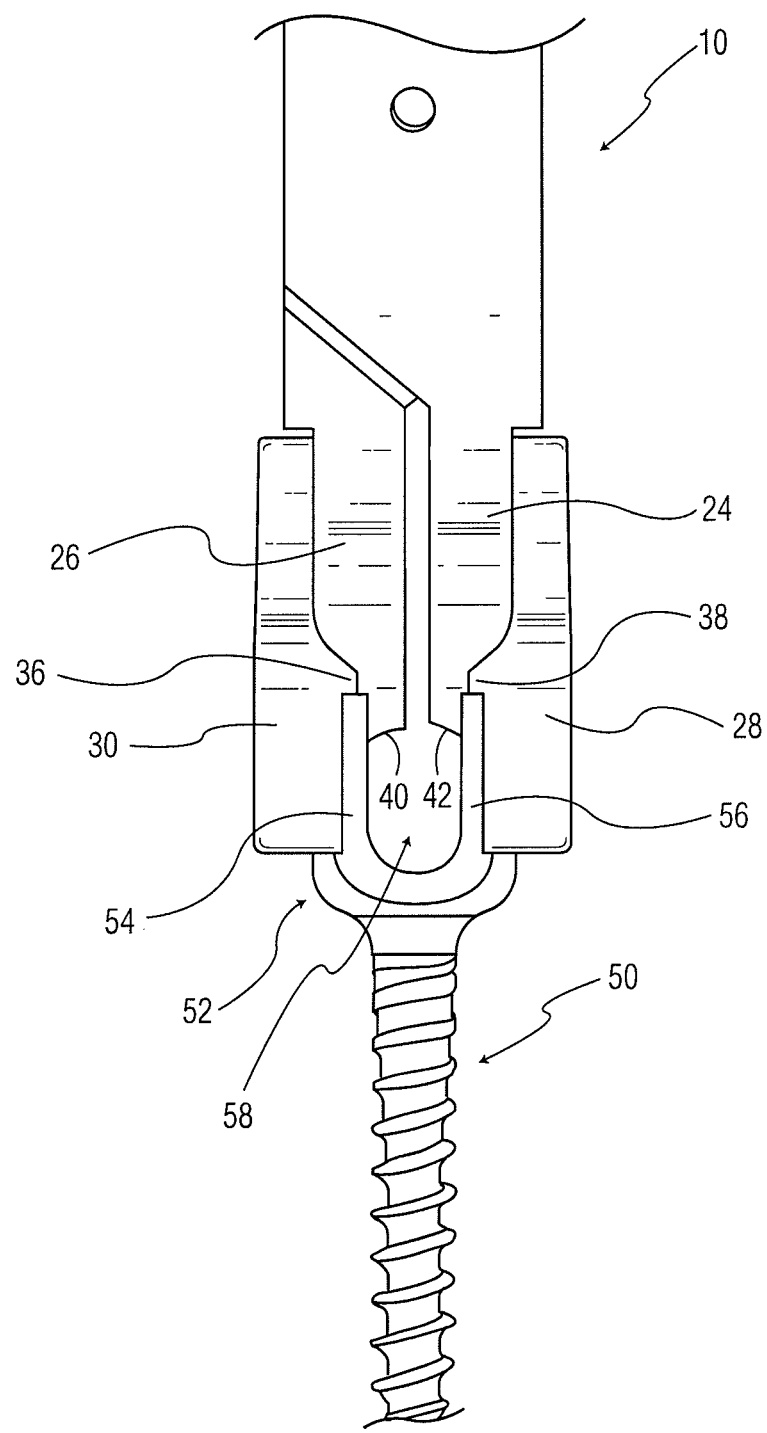
FIG. 3 is a partial front view showing the rod coercer of FIG. 1 in greater detail.

FIG. 3 is a partial front view showing the rod coercer 10 in greater detail. The arms 24, 26 could include curved surfaces 40, 42 which could be shaped to receive the rod. This facilitates a proper interface between the arms 24, 26 as they bear against a rod during reduction of the rod into the implant 50. The shape of the curved surfaces 40, 42 could be varied to accommodate the geometry of the rod. It is noted that the arms 24, 26 need not extend at an angle to the branches 12, 14. Indeed, the arms 24, 26 could be parallel to the branches 12, 14. Additionally, the shapes and angles of the arms 24, 26 could be modified so that the arms 24, 26 can contact the rod at any desired location. It is also noted that a single arm could be provided for contacting the rod to reduce it into an implant.

The shoulders 36, 38, if provided, abut opposed upright walls 54, 56 of the head 52 of the implant 50 when the arms 28, 30 are clamped against the walls 54, 56 of the head 52. The shoulders 36, 38 help to prevent the rod coercer 10 from moving with respect to the implant 50 when the head 52 is clamped by the arms 28, 30. It is noted that the arms 28, 30 and walls 54, 56 could include complementary mechanical engagements (e.g., in the form of protrusions and corresponding recesses, etc.) which prevent movement between the arms 28, 30 and the implant 50 when the head 52 is clamped by the arms 28, 30. Such a protrusion is shown in FIG. 6B, discussed below, and could be provided in any desired geometry. The walls 54, 56 define a channel 58 into which a surgical rod is reduced by the arms 24, 26.

Figure 4A:
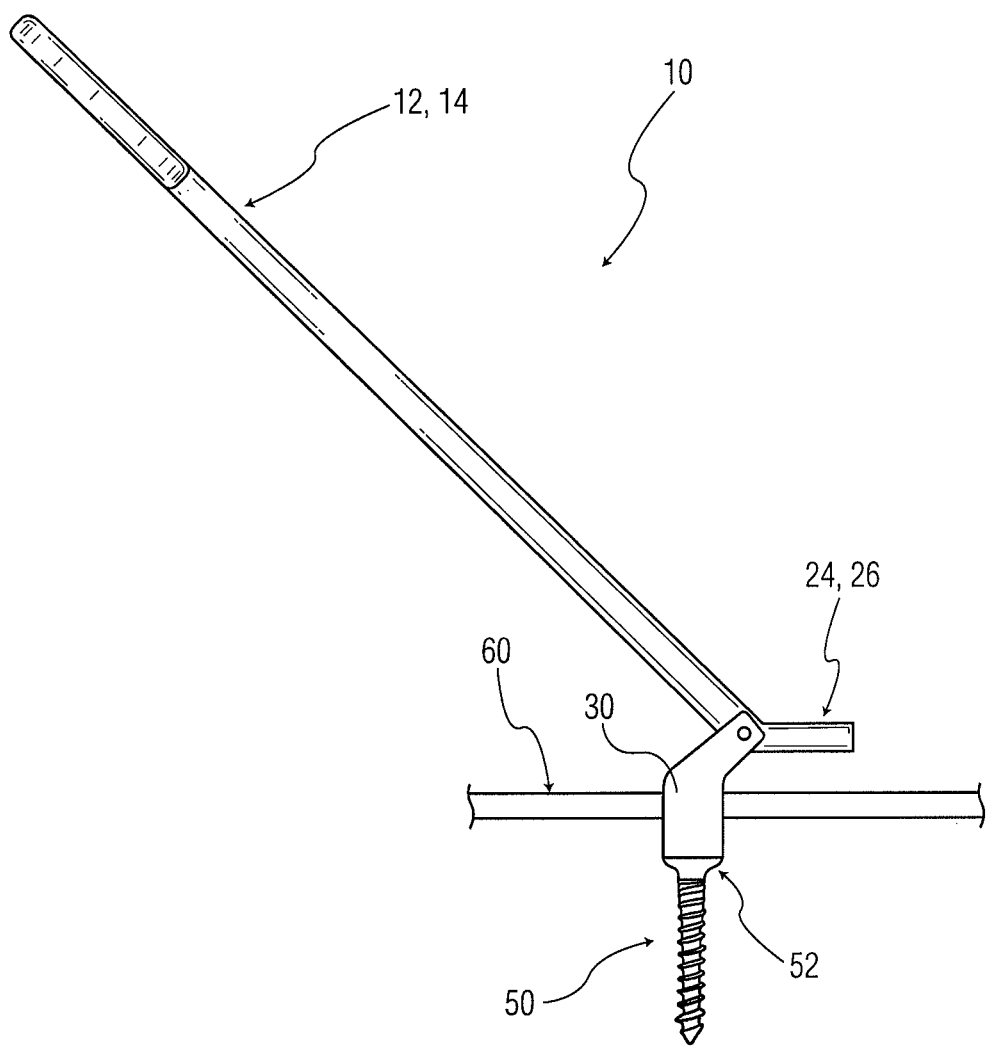
FIGS. 4A-4C are side views showing operation of the rod coercer of FIG. 1 to reduce a surgical rod into the head of an implant.
Figure 4B:
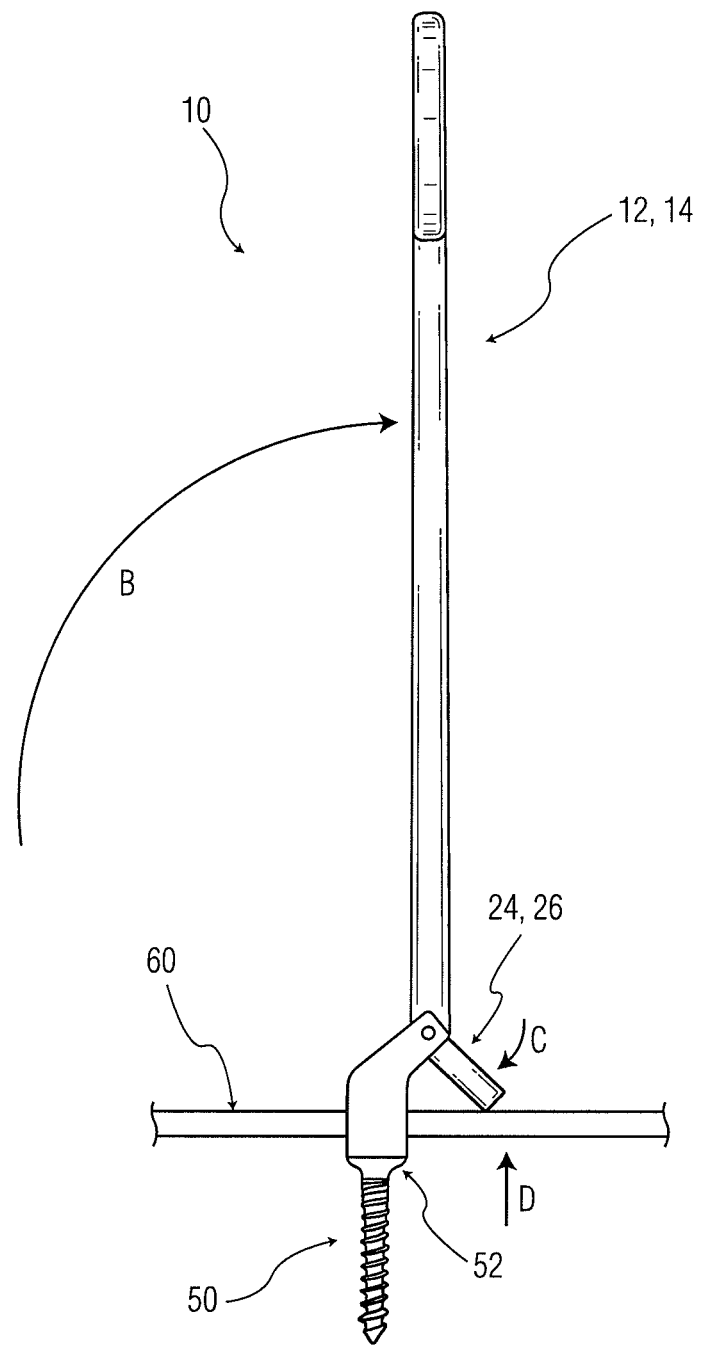
Figure 4C:
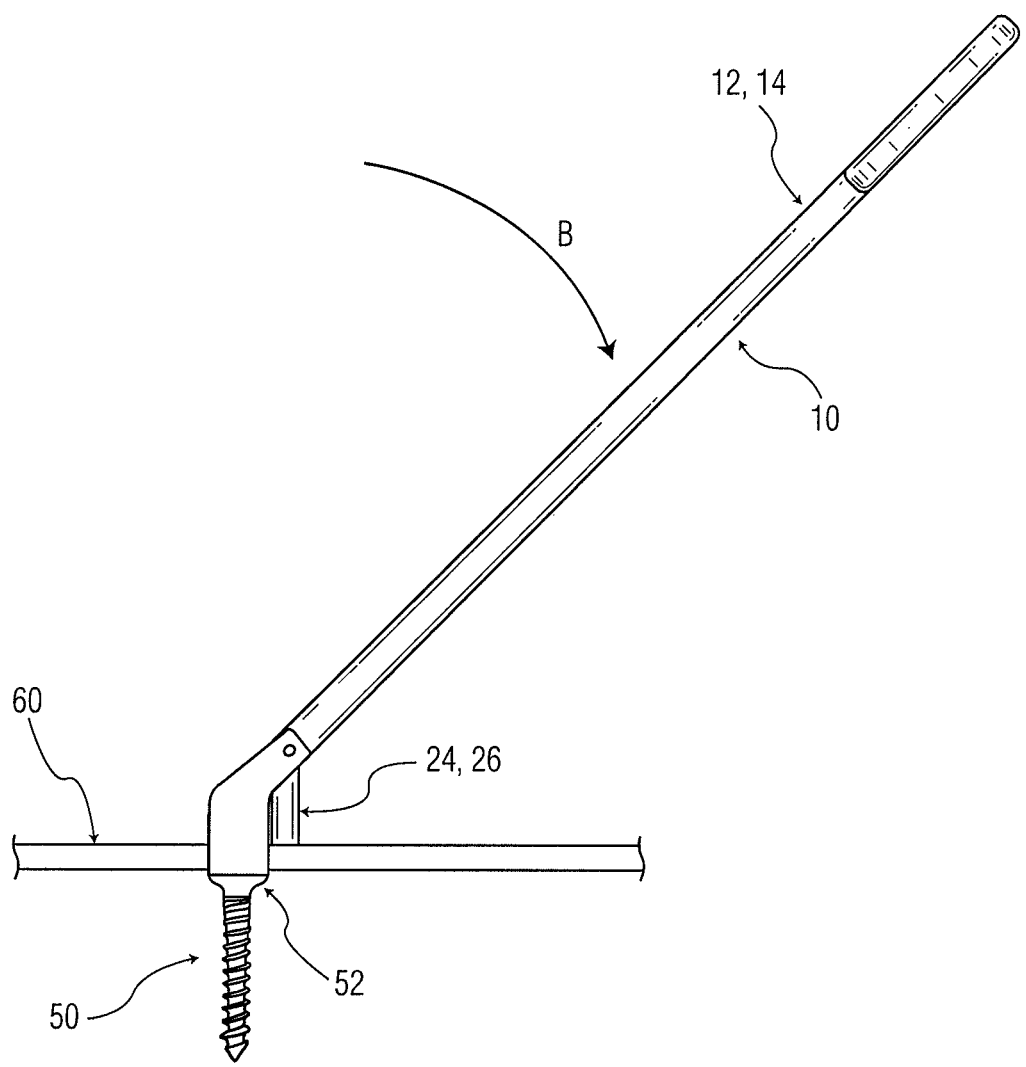

FIGS. 4A-4C are side views showing operation of the rod coercer 10 to reduce a surgical rod 60 into the head 52 of the rod 50. First, as shown in FIG. 4A, the arms 28, 30 of the rod coercer 10 are clamped against the head 52 of the implant 50 in the manner discussed above, such that the rod 60 is positioned between the arms 28, 30 and the arms 24, 26 are positioned above the rod 60. As can be seen, the implant gripping arms 28, 30 and the rod contacting arms 24, 26 define a first angle with respect to each other. Then, as shown in FIG. 4B, the forceps branches 12, 14 are pivoted in the direction shown by arrow B. This causes the arms 24, 26 to move downwardly in the direction shown by arrow C, so that the arms 24, 26 contact and exert force against the rod 60. As can be seen, when the branches 12, 14 are pivoted, a second angle (different than the first angle shown in FIG. 4A) is defined between the implant gripping arms 28, 30 and the rod contacting arms 24, 26. The implant 50 (and an anatomical structure, such as a vertebral body, in which the implant 50 is installed) is then moved upwardly toward the rod 60, as shown by arrow D. It is noted that the rod 60 could also be moved downwardly toward the implant 50, i.e., in a direction opposite the direction shown by arrow D. Thus, the arms 24, 26 operate as levers for moving the implant 50. Finally, as shown in FIG. 4C, the branches 12, 14 are further pivoted in the direction of arrow B, so that the arms 24, 26 are urged to a final position against the rod 60. In this position, the rod 60 is reduced into the head 52 of the implant 50, and a threaded cap or other type of locking device can be installed into the head 52 of the implant 50 to lock the rod 60 in position in the head 52. Once the rod is locked with respect to the implant 50 using a suitable locking device, the rod coercer 10 can be removed from the implant 50 by pivoting the forceps branches 12, 14 away from each other.

Figure 5A:
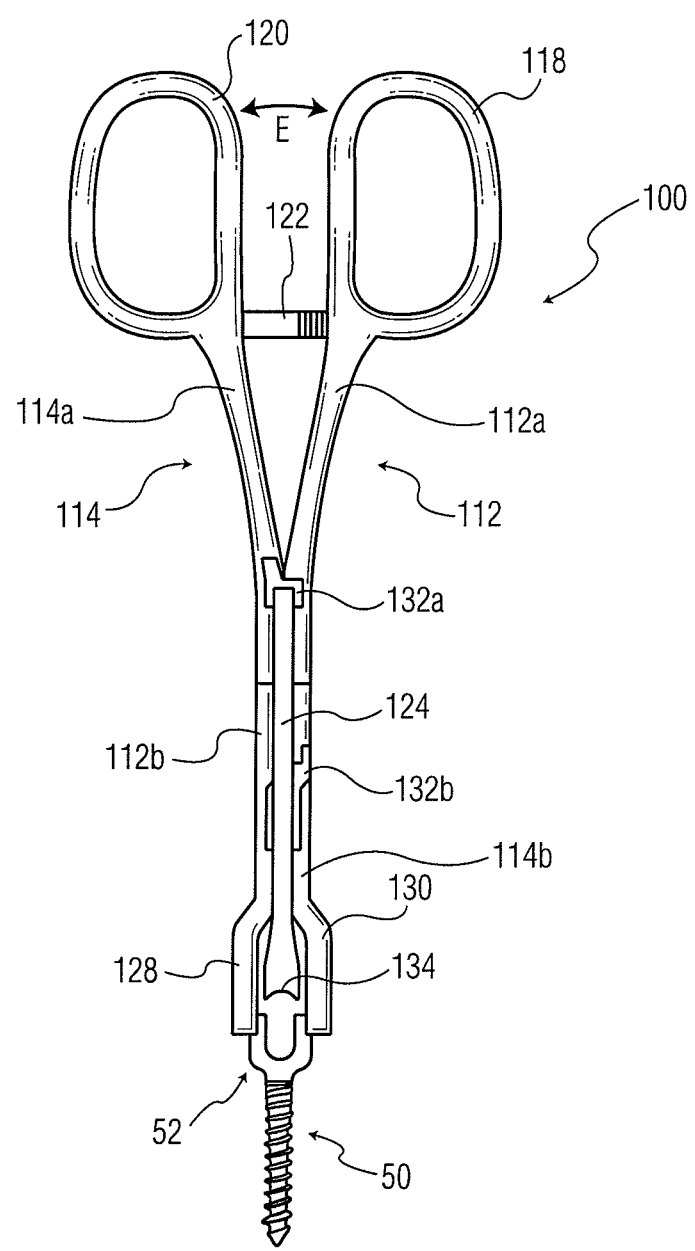
FIGS. 5A-5C are rear and side views of another embodiment of the rod coercer of the present invention, which includes pivotable upper and lower forceps branches and a rod contacting arm interconnected therewith.
Figure 5B:
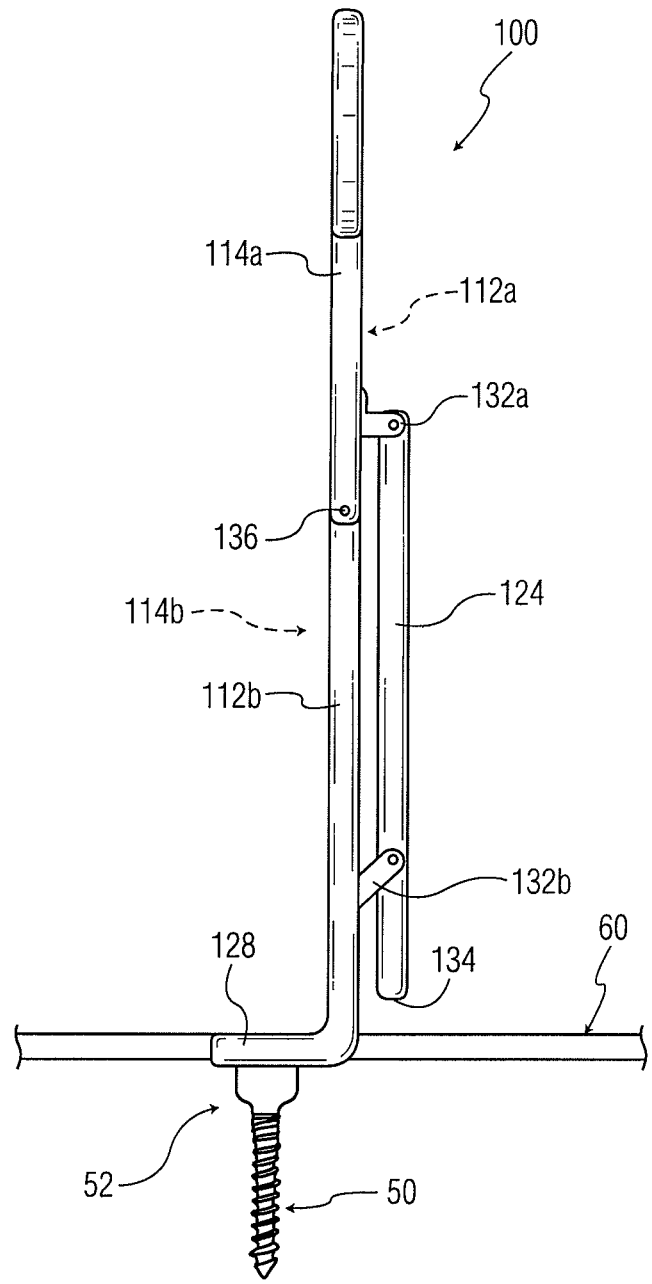
Figure 5C:
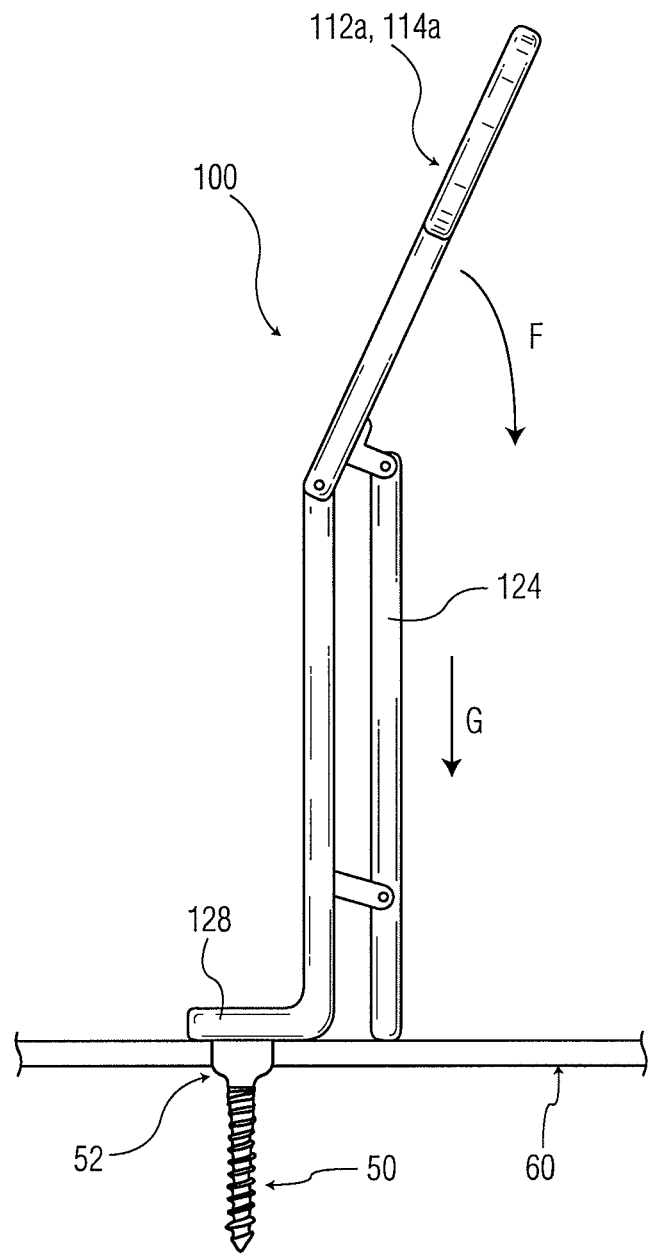

FIGS. 5A-5C are rear and side views of another embodiment of the rod coercer of the present invention, indicated generally at 100. The rod coercer 100 includes forceps branches 112, 114 which are pivotally interconnected and which can be pivoted with respect to each other, in the direction shown by arrow E. The branch 112 is divided into upper and lower branch portions 112a, 112b which pivot with respect to each other, and the branch 114 is divided into upper and lower branch portions 114a, 114b which pivot with respect to each other. Implant gripping arms 128, 130 are provided at the ends of the lower branch portions 112b, 114b for gripping opposite sides of the head 52 of the implant 50, and finger loops 118, 120 are provided at opposite ends of the branches 112, 114 for receiving an operator's fingers. The gripping arms 128, 130 can be brought together to clamp the head 52 of the implant 50 by urging the branches 112, 114 together in the direction of arrow E. Corresponding locking tabs 122 could be provided to lock the branches 112, 114 together, which locks the gripping arms 128, 130 against the head 52 of the implant 50. Upper and lower linkages 132a, 132b link a rod contacting arm 124 to the upper and lower branch portions 114a, 114b of the forceps branch 114. Of course, the linkages 132a, 132b could be attached to the upper and lower branch portions 112a, 112b of the forceps branch 112.

As shown in FIG. 5B, an upper end of the rod contacting arm 124 is pivotally interconnected to the upper branch portion 114a by the linkage 132a, such that the linkage 132a is fixedly attached at one end to the upper branch portion 114a and pivotally attached at an opposite end to the rod contacting arm 124. The lower end of the rod contacting arm 124 is linked to the lower branch portion 114b by the linkage 132b, such that the linkage 132b is pivotally attached at one end to the lower branch portion 114b and pivotally attached at an opposite end to the rod contacting arm 124. A curved surface 134 could be provided at the bottom of the rod contacting arm 124, which could be shaped to match the shape of the rod 60.

The upper and lower branch portions 112a, 114a and 112b, 114b are pivotally interconnected by a pivotable interconnection 136 provided in each branch 112, 114, which allows the upper branch portions 112a, 114a to pivot with respect to the lower branch portions 112b, 114b, as shown by arrow F in FIG. 5C. Such movement causes the rod contacting arm 124 to move downwardly in the general direction indicated by arrow G, so that the rod contacting arm 124 contacts the rod 60. This causes the implant 50 (and an anatomical structure in which it is installed, such as a vertebral body) to be drawn upwardly toward the rod 60, so as to reduce the rod 60 into the head 52 of the implant 50. It is also noted that the rod contacting arm could cause the rod 60 to move downwardly toward the implant 50 to reduce the rod 60 into the head 52 of the implant 50.

Figure 6A:
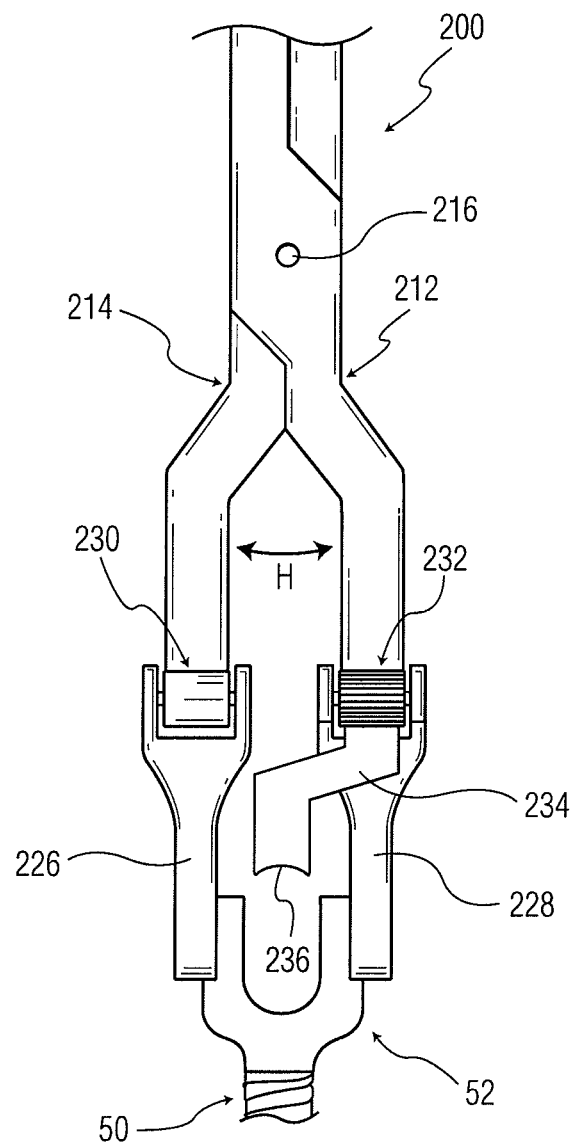
FIGS. 6A-6C are partial rear, perspective, and side views of another embodiment of the rod coercer of the present invention, which includes pivotable implant gripping arms and a geared rod contacting arm.
Figure 6B:
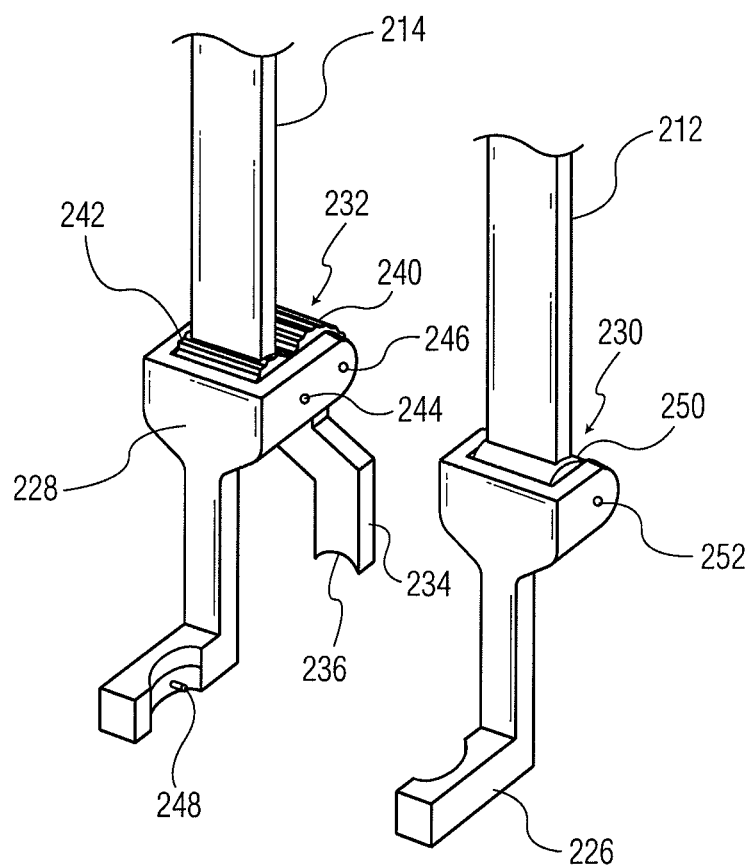
Figure 6C:
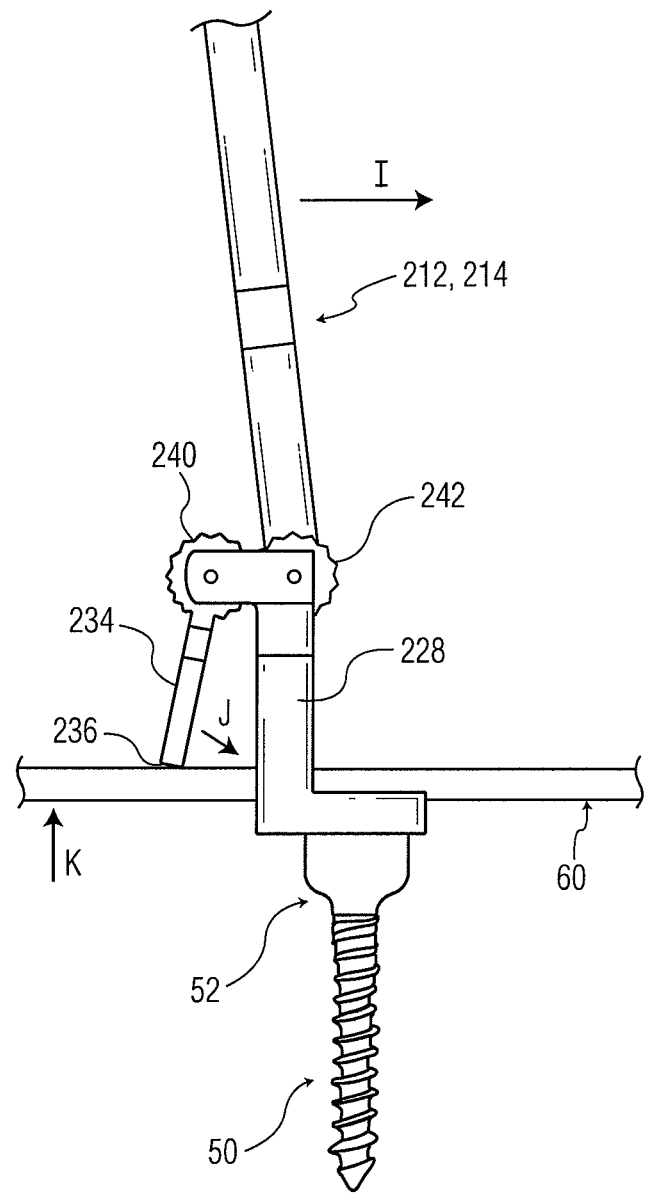

FIGS. 6A-6C are partial rear, perspective, and side views of another embodiment of the rod coercer of the present invention, indicated generally at 200. As shown in FIG. 6A, the rod coercer 200 includes branches 212, 214 which are pivotally interconnected via pivotable interconnection 216 and which can be pivoted with respect to each other, in the direction of arrow H. Upper ends of the branches 212, 214 could include finger loops and, optionally, locking tabs, such as the finger loops and locking tabs shown in the previous embodiments. Implant gripping arms 226, 228 are provided for gripping opposite sides of the head 52 of the implant 50, and can be brought together to clamp the head 52 of the implant 50 by urging the branches 212, 214 together in the direction of arrow H.

As shown in FIG. 6B, the implant gripping arms 226, 228 are pivotally interconnected with the branches 212, 214 via joints 230, 232. The joint 230 is formed by a collar 250 attached to an end of the branch 212, which pivots about a pin 252 extending through the upper portion of the gripping arm 226. The joint 232 links a rod contacting arm 234 to the forceps branch 214. The branch 214 is attached to a face of a forceps gear 242, and the rod contacting arm 234 is attached to the face of an arm gear 240, both of which gears 240, 242 intermesh. The gears 240, 242 rotate about pins 244, 246 inserted into an upper end of the implant gripping arm 228. Thus, both the forceps branch 214 and the rod contacting arm 234 pivot at adjacent pivot points in joint 232.

Optionally, protrusions 248 could be provided on the rod contacting arms 226, 228 for insertion into corresponding recesses formed on an implant. The geometry of such protrusions could be varied as desired. Also, the rod contacting arm 234 could be bent (as shown in FIG. 6B) or provided in any desired shape or geometry. Additionally, a curved surface 236, shaped to match the shape of a rod, could be provided on the rod contacting arm 234.

As shown in FIG. 6C, when the branches 212, 214 are pivoted in the direction of arrow I, the forceps gear 242 rotates. This causes the arm gear 240 to rotate, which causes the rod contacting arm 234 to pivot in the direction of arrow J, so that the surface 236 contacts the rod 60. This causes the implant 50 (and an anatomical structure (e.g., a vertebral body) into which the implant 50 is installed) to be drawn upwardly toward rod 60 by the implant gripping arms 228, 230, as indicated by arrow K, so that the rod is reduced into the head 52 of the screw 50. It is noted that the rod 60 could also be urged downwardly toward the screw 50 to reduce the rod 60 into the head 52 of the screw 50.

Figure 7:
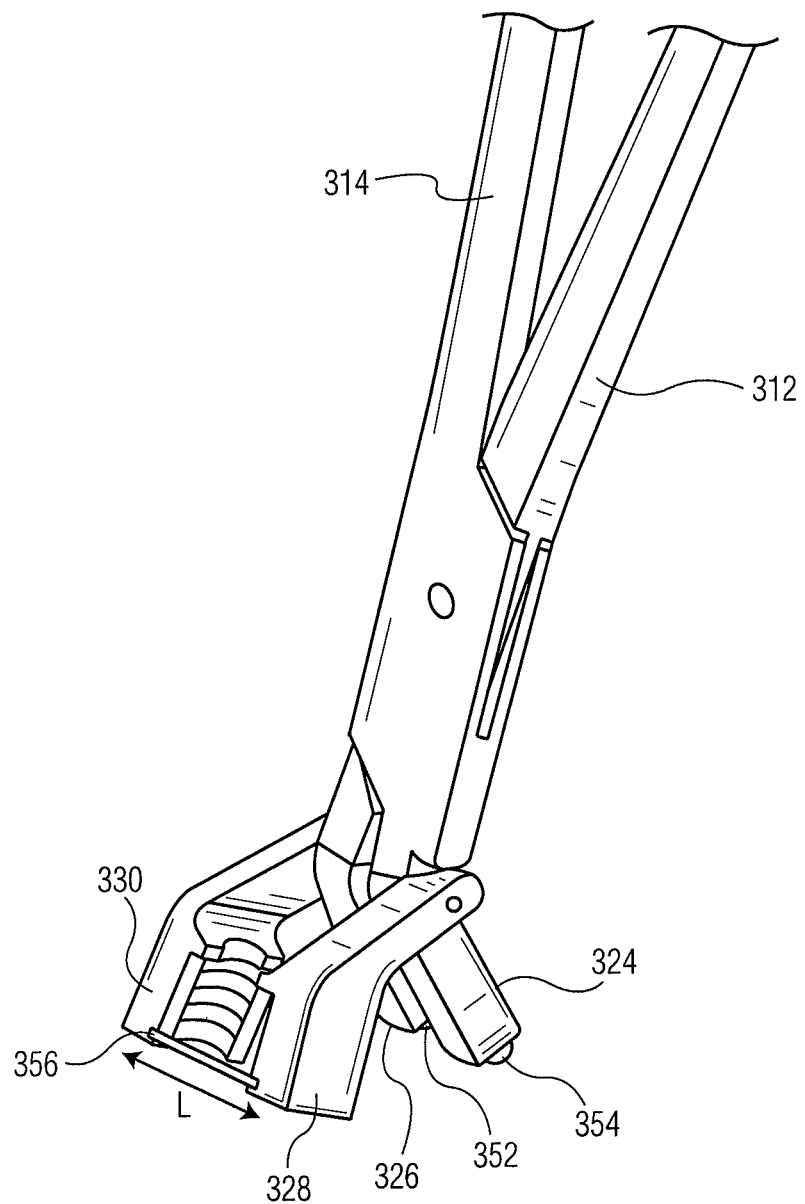
FIG. 7 is a perspective view showing another embodiment of the rod coercer of the present invention, wherein integral rollers are provided at ends of the rod contacting arms and a retainer interconnects the implant gripping arms to maintain the arms in facing relationship.

FIG. 7 is a perspective view showing another embodiment of the present invention, which is similar in construction to the rod coercer shown in FIGS. 1-4C. In this embodiment, integral rollers 352, 354 are provided on ends of the rod contacting arms 324, 326, which roll along a rod as it is reduced. The rollers 352, 354 reduce friction between the rod and the arms 324, 326, thereby reducing the amount of force required to reduce a rod. Also provided is a flexible retainer 356 interconnecting the implant gripping arms 328, 330. The retainer 356 allows the arms 328, 330 to be maintained in facing relationship with each other as they are pivoted with respect to forceps branches 312, 314. Also, the retainer 356 stretches (as shown by arrow L) so that the arms 328, 330 can be spread apart by manipulating the forceps branches 312, 314. As such, the retainer 356 does not interfere with operation of the rod coercer. The rollers 352, 354 could be provided on the rod contacting arms of each of the embodiments of the rod coercer disclosed herein, and the flexible member 356 could be provided for interconnecting the implant gripping arms of each embodiment of the rod coercer disclosed herein.

Figure 8:
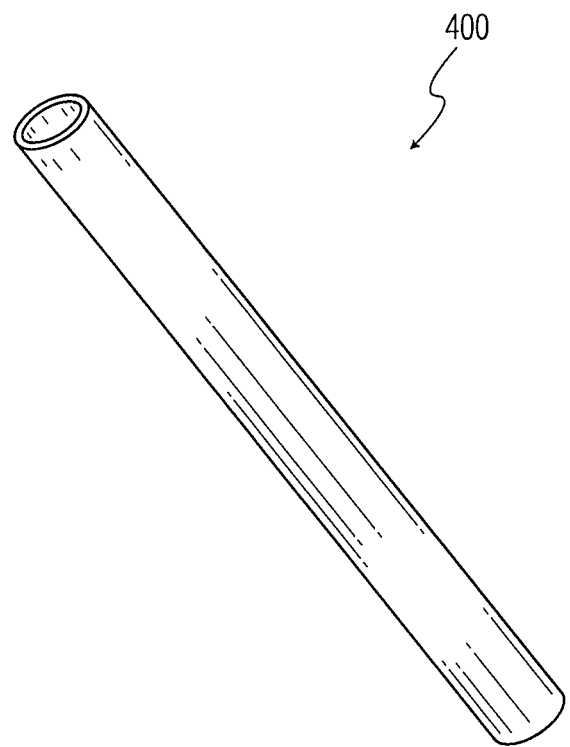
FIG. 8 is a perspective view of a cannula that can be used with the rod coercer of the present invention.

FIG. 8 is a perspective view showing a cannula (guide tube) 400 which could be utilized with each embodiment of the rod coercer of the present invention. The cannula 400 could be positioned between the implant gripping arms of the present invention to guide a set screw and an associated tightening tool for locking a rod into an implant. The shape and size of the cannula 400 could be modified as desired without departing from the spirit or scope of the present invention. It is also noted that the cannula 400 could be threadably, frictionally, or otherwise engaged with the implant gripping arms of the present invention (e.g., using corresponding interlocking protrusions/recesses to lock the cannula 400 to the arms).

Figure 9:
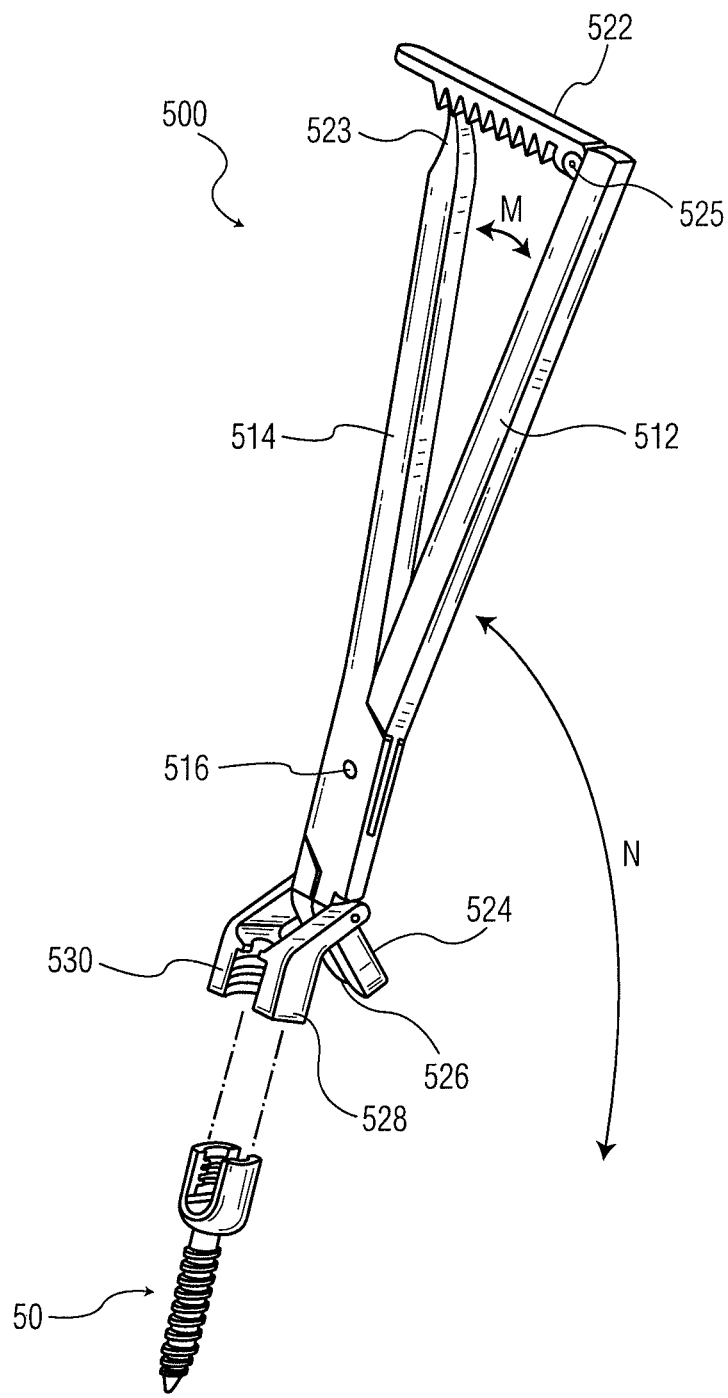
FIG. 9 is a perspective view showing the rod coercer of the present invention, wherein releasable locking means are provided on the handles of the rod coercer.

FIG. 9 is a perspective view showing another embodiment of the rod coercer of the present invention, indicated generally at 500. The rod coercer 500 includes right and left handle branches 512, 514 which are pivotally interconnected at a point 516 (e.g., by a pin extending through and pivotally interconnecting the branches 512, 514, or any other suitable type of pivotable interconnection). The branches 512, 514 include means for releasably locking the branches 512, 514 in a closed and locked position, such as a ratchet mechanism comprising a pivotable toothed lever 522 rotating about a hinge 525 on one handle and a pawl 523 located on the opposite handle. Rod contacting arms 524, 526, which contact a rod to reduce it into an implant, are provided at the ends of the branches 512, 514. Implant gripping arms 528, 530 are pivotally interconnected with the branches 512, 514. The implant gripping arms 528, 530 fixedly grip an implant 50 (which could be a screw (e.g., pedicle screw), hook, or any other suitable implant which is configured to receive a rod), while the rod contacting arms 524, 526 pivot with respect to the implant gripping arms 528, 530 to reduce a rod into the implant 50.

To grip the implant 50, the handle branches 512, 514 are pivoted away from each other about a first axis (in the direction shown by arrow M), which causes the implant gripping arm 528 to move away from the implant gripping arm 530, and consequently, the arms 524, 526 similarly move away from each other. The arms 528, 530 are then positioned about opposite sides of the implant 50, as well as about a rod (not shown in FIG. 9) to be reduced into the implant 50. The handle branches 512, 514 are then urged toward each other in the direction shown by arrow M, by an operator's hand applying force to the branches 512, 514, so that the arms 528, 530 fixedly clamp the implant 50 and, consequently, the arms 524, 526 are brought together. The gripping arms 528, 530 each have inner surfaces which could be cylindrical in shape or could have any other shape configured to grip or hold the implant 50. The inner surfaces contact the sides of the implant 50 and are held in a fixed position against the implant 50 when the arms 528, 530 are clamped against the implant 50. When the arms 528, 530 are clamped against the implant 50, the handle branches 512, 514 can pivot with respect to the arms 528, 530, in the direction shown by arrow N. As discussed herein, this motion (similar to the motion shown by arrow B in FIGS. 1 and 4B-4C) allows for reduction of a rod into the implant 50.

To utilize the ratchet mechanism, as the branches 512, 514 are urged together, the pawl 523 moves with respect to the teeth of the lever 522 until the branches 512, 514 stop moving and the pawl 523 settles against one of the teeth of the lever 522. The teeth of the lever 522 are shaped such that after the branches 512, 514 are urged together, the teeth retain the pawl 523 in a fixed position, thereby locking the branches 512, 514 together. This locks of the handles 512, 514 in position as the implant gripping arms 528, 530 hold the implant 50. The coercer 500 can be released from the implant 50 by pivoting the lever 522 upwardly, so that the pawl 523 disengages from the lever 522.

It is noted that the ratchet mechanism shown in FIG. 9 could be substituted with any other suitable means for releasably locking the handle branches 512, 514, such as a screw that releasably locks the handle branches 512, 514, or any other suitable type of interconnection.

Figure 10A:
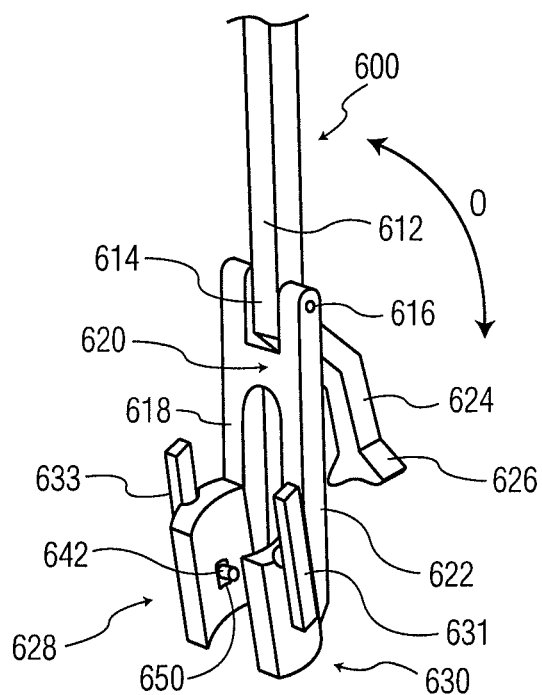
FIGS. 10A-11D are perspective, side, and cross-sectional views showing another embodiment of the rod coercer of the present invention which includes a single handle and spring-loaded implant gripping levers for releasably locking the rod coercer to an implant.
Figure 10B:
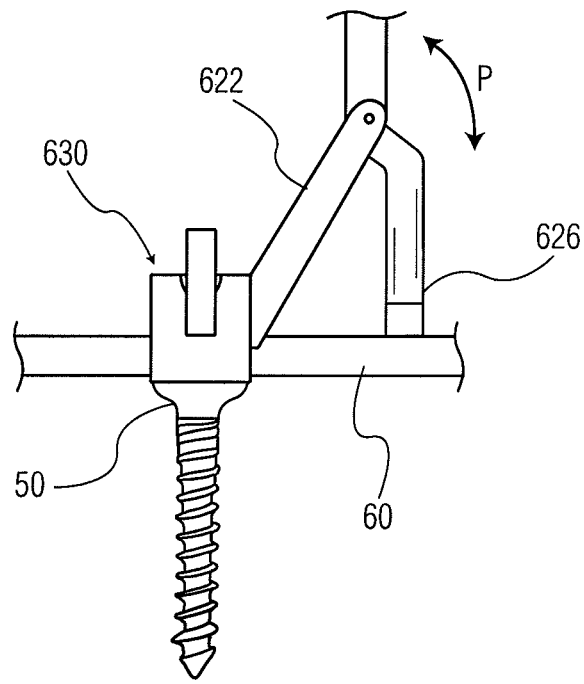

FIGS. 10A-11D are perspective, side, and cross-sectional views showing another embodiment of the rod coercer of the present invention, indicated generally at 600, having a single handle 612 and spring-loaded implant gripping levers 631, 633. As shown in FIGS. 10A-10B, the rod coercer 600 includes a single handle 612 which is pivotally interconnected with an implant gripping assembly 620 at a pivot point 614 via a pin 616, allowing the assembly 620 to be pivoted in the direction shown by arrow O. One end of the handle 612 includes a rod contacting arm 624 and a curved rod-contacting surface 626. Spring-loaded implant gripping levers 631, 633 are provided on implant gripping arms 628, 630, which are attached to extension arms 618, 622. The gripping arms 628, 630 are affixed to each other by a bridge 620 which connects the extension arms 618, 622.

Figure 10C:
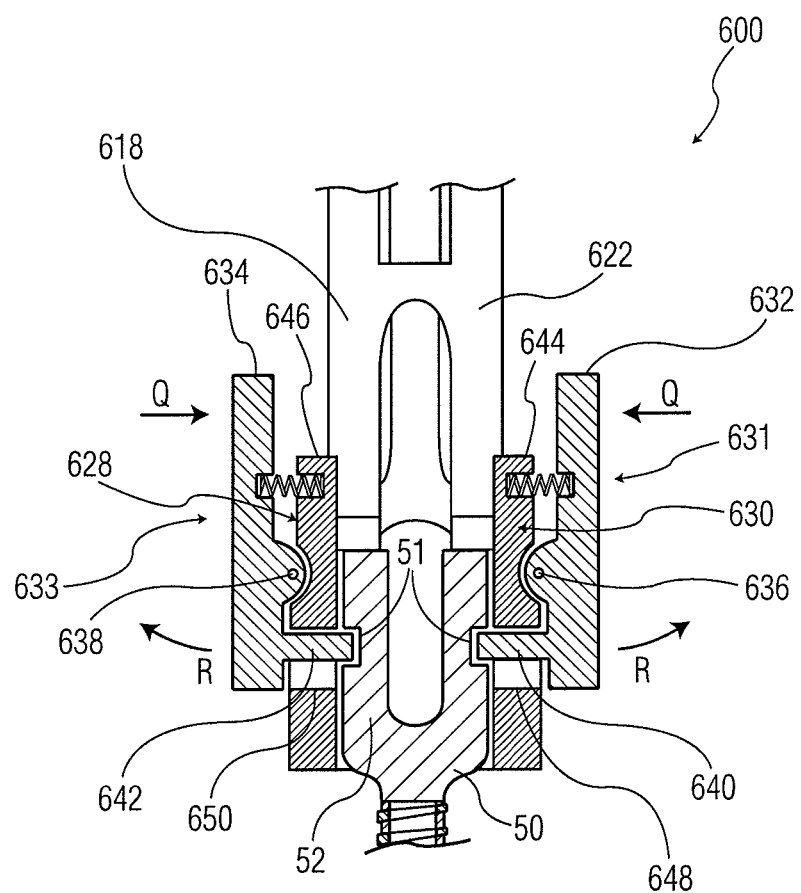

As shown in FIG. 10C, the spring-loaded locking levers 631, 633 are connected to the implant gripping arms 628, 630 by hinges 636, 638. Springs 644, 646 bias upper ends 632, 634 of the levers 631, 633 away from the arms 628, 630, forcing projections 640, 642 through apertures 648, 650 in the arms 628, 630, and causing the projections 640, 642 to engage recesses 51 in the head 52 of the implant 50 to lock the arms 628, 630 in position on sides of the implant 50. To engage the arms 628, 630 with the implant 50, the upper ends 632, 634 of the locking levers 631, 633 are first pressed in the direction shown by arrows Q. This causes the protrusions 640, 642 to retract from the apertures 648, 650, as shown by arrows R. Then, the arms 628, 630 are positioned about the head 52 of the implant 50, and the implant gripping levers 632, 634 are released by the operator. The springs 646, 648 urge the protrusions 640, 642 through the apertures 648, 650 and into the recesses 51, thereby fixedly engaging the arms 628, 630 (and, thus, the rod coercer 600) to the implant 50. To disengage the coercer 600 from the implant 50 (after rod reduction), the upper ends 632, 634 of the levers 631, 633 are depressed, resulting in the disengagement of the projections 640, 642 from the recesses 51 in the direction shown by arrows R. Optionally, the protrusions 640, 642 may be angled or rounded so that the implant gripping arms 628, 630 can be pushed directly on to the implant head 52 to obviate the need to depress the upper ends 632, 634.

Optionally, the spring-loaded implant gripping levers can be L-shaped, as shown in FIGS. 11A-D. As shown therein, the rod coercer 600 includes a single handle 712 which is pivotally interconnected with an implant gripping assembly 720 at a pivot point 714 via a pin 716, allowing the assembly 720 to be pivoted in the direction shown by arrow S. One end of the handle 712 includes a rod contacting arm 724 and a curved rod-contacting surface 726. L-shaped, spring-loaded implant gripping levers 731, 733 are provided on implant gripping arms 728, 730, which are attached to extension arms 718, 722. The gripping arms 728, 730 are affixed to each other by a bridge 720 which connects the extension arms 718, 722.

Figure 11A:
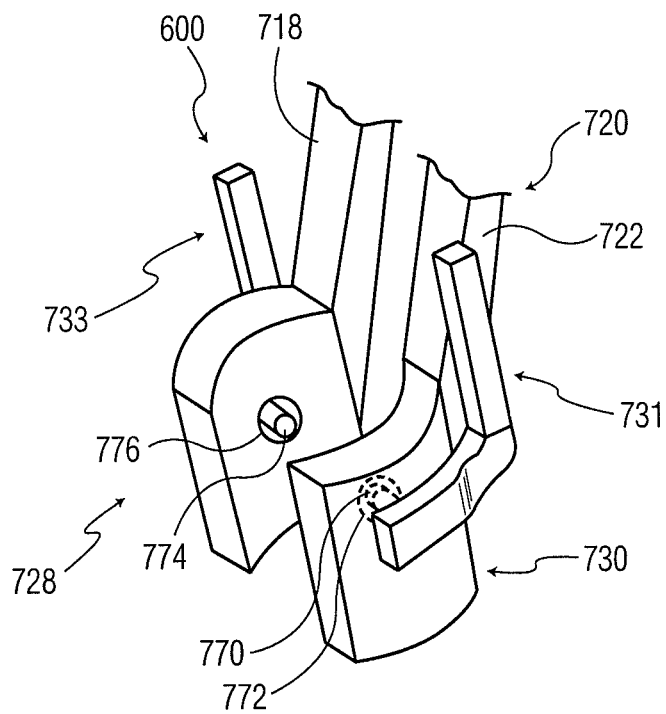
Figure 11B:
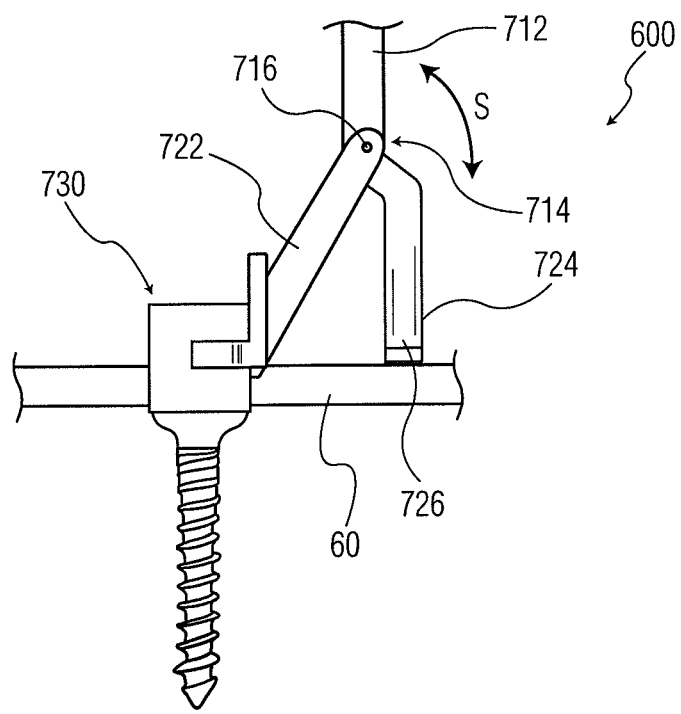
Figure 11C:
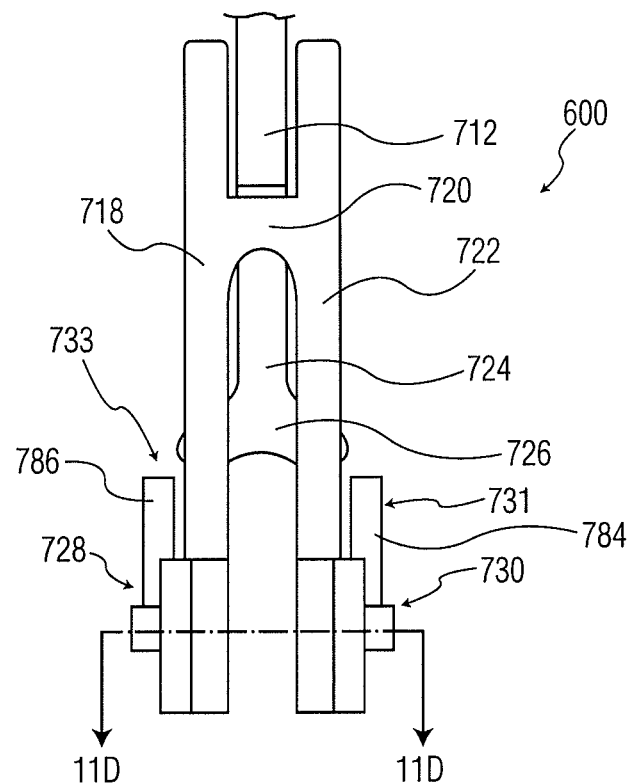
Figure 11D:
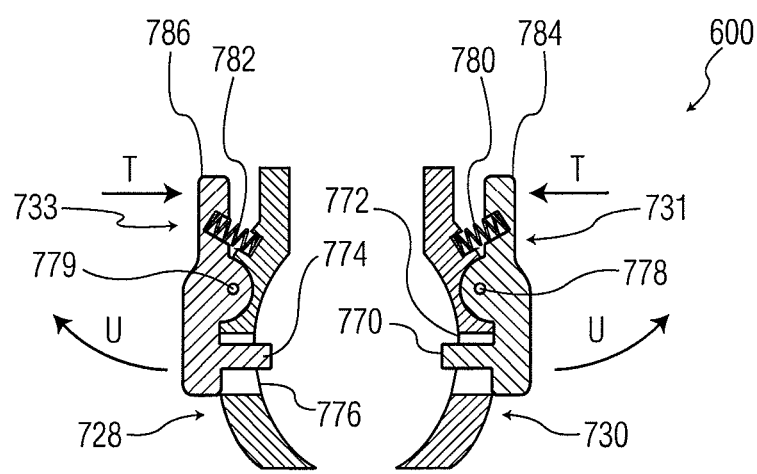

As shown in FIG. 11D, the spring-loaded locking levers 731, 733 are interconnected to the implant gripping arms 728,

730 by hinges 778, 779. Springs 780, 782 bias ends 784, 786 of the levers 731, 733 away from the arms 728, 730, forcing projections 770, 774 through apertures 772, 776 in the arms 728, 730, and causing the projections 770, 774 to engage recesses in the head of an implant (see, e.g., implant 50 discussed above) to lock the arms 728, 730 in position on sides of the implant. To engage the arms 728, 730 with the implant, the ends 784, 786 of the levers 731, 733 are first pressed in the direction shown by arrows T. This causes the protrusions 770, 774 to retract from the apertures 772, 776, as shown by arrows U. Then, the arms 728, 730 are positioned about the head of the implant, and the ends 784, 786 of the implant gripping levers 731, 733 are released by the operator. The springs 780, 782 urge the protrusions 770, 774 through the apertures 772, 776 and into the recesses, thereby fixedly engaging the arms 728, 730 (and, thus, the rod coercer 600) to the implant 50. To disengage the coercer 600 from the implant 50 (after rod reduction), the ends 784, 786 of the levers 731, 733 are depressed, resulting in the disengagement of the protrusions 770, 774 from the recesses in the direction shown by arrows U. Optionally, the protrusions 770, 774 may be angled or rounded so that the implant gripping arms 728, 730 can be pushed directly on to the implant head to obviate the need to depress the ends 784, 786.

Figure 12A:
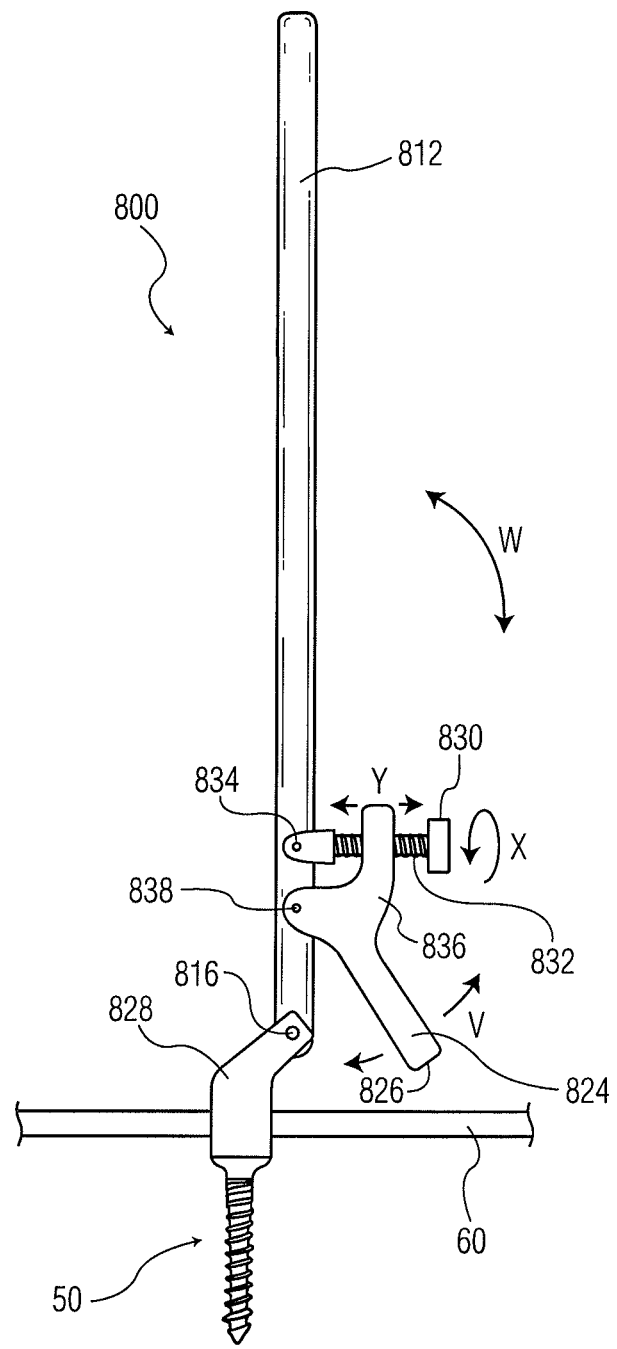
FIGS. 12A-13B are side and cross-sectional views of another embodiment of the rod coercer of the present invention in greater detail, wherein an adjustable rod contacting arm assembly is provided.
Figure 12B:
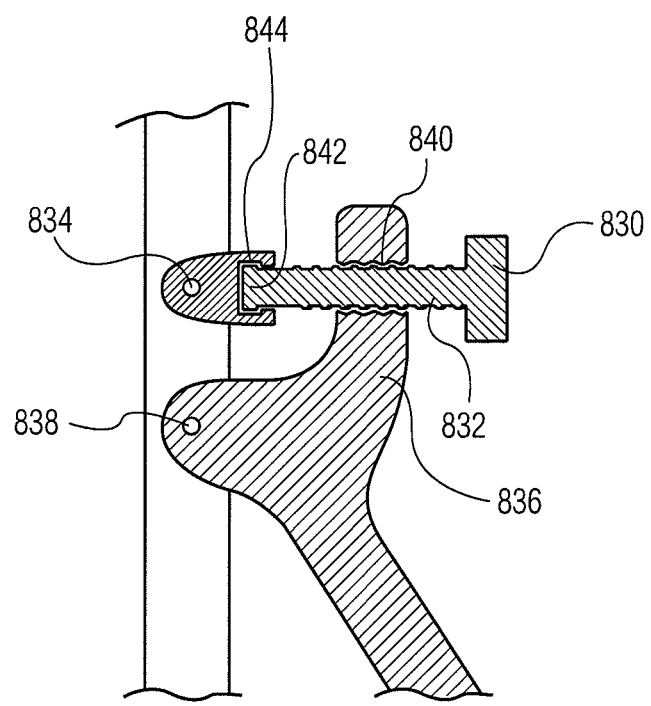

FIGS. 12A-12B are side views of another embodiment of the rod coercer of the present invention, indicated generally at 800, which includes a rod contacting arm having an adjustable angle with respect to a handle. The rod coercer 800 includes a handle 812 which is pivotally interconnected with an implant gripping assembly 828 at a pivot point 816 and can be pivoted in the direction shown by arrow W. The implant gripping assembly 828 could include any of the implant gripping arm configurations (and associated levers, protrusions, hinges, etc.) disclosed herein, or it could even include a single, cylindrical sleeve with internal, spring-loaded protrusions which permit the assembly 828 to be pushed onto the head of the screw 50 and releasably coupled thereto. Located on handle 812 are two more pivot points 834, 838. The first pivot point 834 is connected to a linkage 844 and associated knob 830. The knob 830 includes a threaded shaft 832 and a terminal end 842 rotatably captured within the linkage 844. The threaded shaft 832 is threadably engaged with a threaded aperture 840 in an upper portion 836 of rod contacting arm 824. The second pivot point 838 is connected to the rod contacting arm 824, which includes a curved surface 826 to accommodate the geometry of a rod to be reduced.

As shown in FIG. 12B, the threaded shaft 832 remains in permanent mechanical communication with threaded orifice 840 of the adjustment arm 836. Rotation of the knob 830 (as shown by arrow X in FIG. 12A) causes mechanical interaction between the threaded shaft 832 and the threaded orifice 840, resulting in movement of the upper portion 836 of the rod contacting arm 824 along the threaded shaft 832, as shown by arrow Y of FIG. 12A. This movement can be in either direction, depending on clockwise or counter-clockwise rotation of the knob 830. This movement results in movement of rod contacting arm 824, along the direction shown by arrow V of FIG. 12A. Such movement allows the rod contacting arm 824 to be adjusted to a desired location and angle, whereupon the handle 812 can then be rotated downward in the general direction indicated by arrow W to bring rod contacting arm 824 in contact with the rod 60. This causes the implant 50 and the rod 60 to be drawn together, so as to reduce the rod 60 into the head 52 of the implant 50. It is also noted that the rod contacting arm could cause the rod 60 to move downwardly toward the implant 50 to reduce the rod 60 into the head 52 of the implant 50.

Figure 13A:
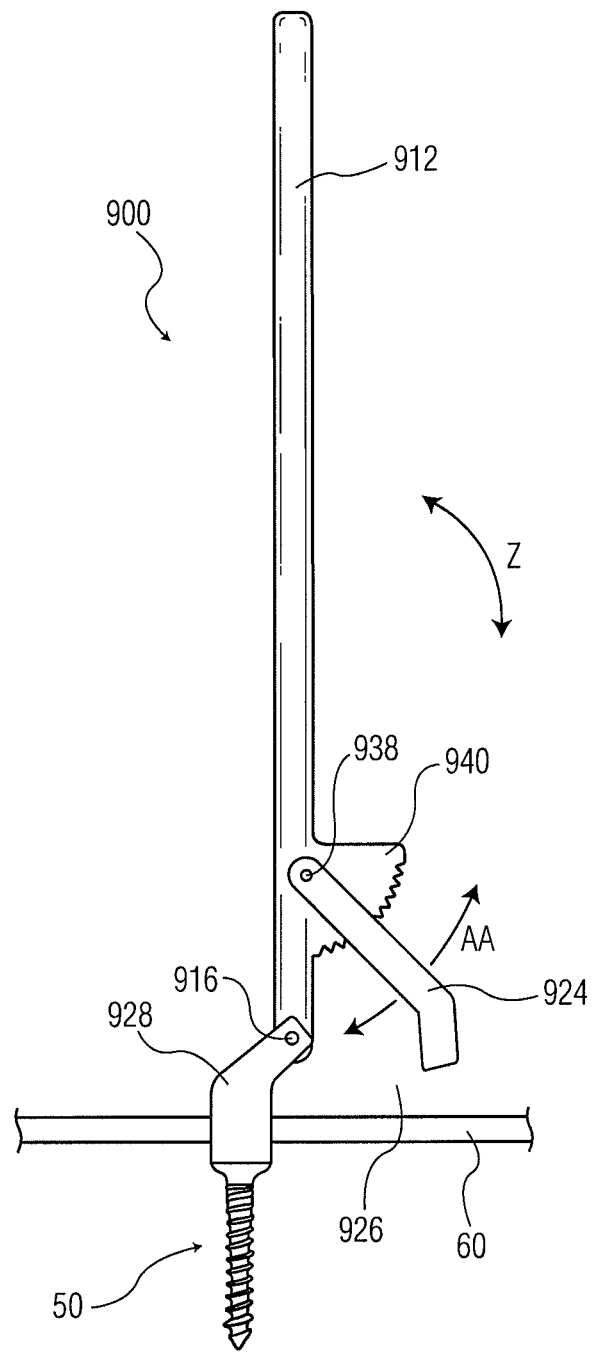
Figure 13B:
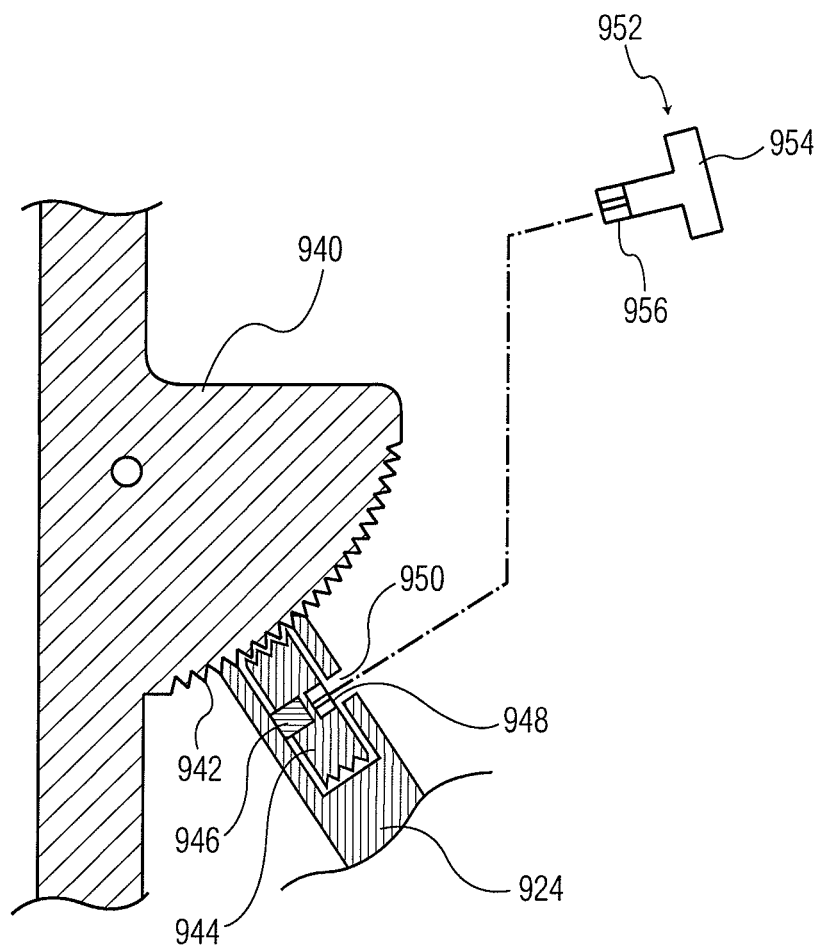

FIGS. 13A-13B are side views of another embodiment of the rod coercer of the present invention in greater detail, indicated generally at 900, which includes an adjustable rod contacting arm. The rod coercer 900 includes a handle 912 which is pivotally interconnected with an implant gripping assembly 928 at a pivot point 916 and can be pivoted in the direction shown by arrow Z. Located on the handle 912 is a second pivot point 938. The second pivot point 938 allows for the rotation of the adjustable rod contacting arm 924 in the general direction show by arrow AA through a fixed partial gear 940 and a worm gear 944.

The angle of the adjustable rod contacting arm 924 can be adjusted by rotating a worm gear 944 provided in the rod contacting arm 924, as shown in FIG. 13B. The partial gear 940 includes teeth 942 in mechanical communication with helical grooves of the worm gear 944 of the contacting arm 924. The worm gear 944 is connected to the contacting arm 924 by a spindle 946 which allows for rotation of the gear. Of course, any other suitable way of capturing the gear 944 within the rod contacting arm 924 could be provided. Rotation of the gear 944 is achieved using a key 952 which can be inserted through an aperture 950 of the contacting arm 924 and turned. This causes the grooves of the worm gear to move along the teeth of the fixed gear 940, resulting in the movement of the rod contacting arm 924 along the fixed gear 940, as shown by arrow AA. This allows the arm 924 to be moved to a desired angle, whereupon the handle 912 can then be rotated downward, in the general direction indicated by arrow Z, to bring the rod contacting arm 924 in contact with the rod 60. This causes the implant 50 and the rod 60 to be drawn together, so as to reduce the rod 60 into the head 52 of the implant 50.

Figure 14A:
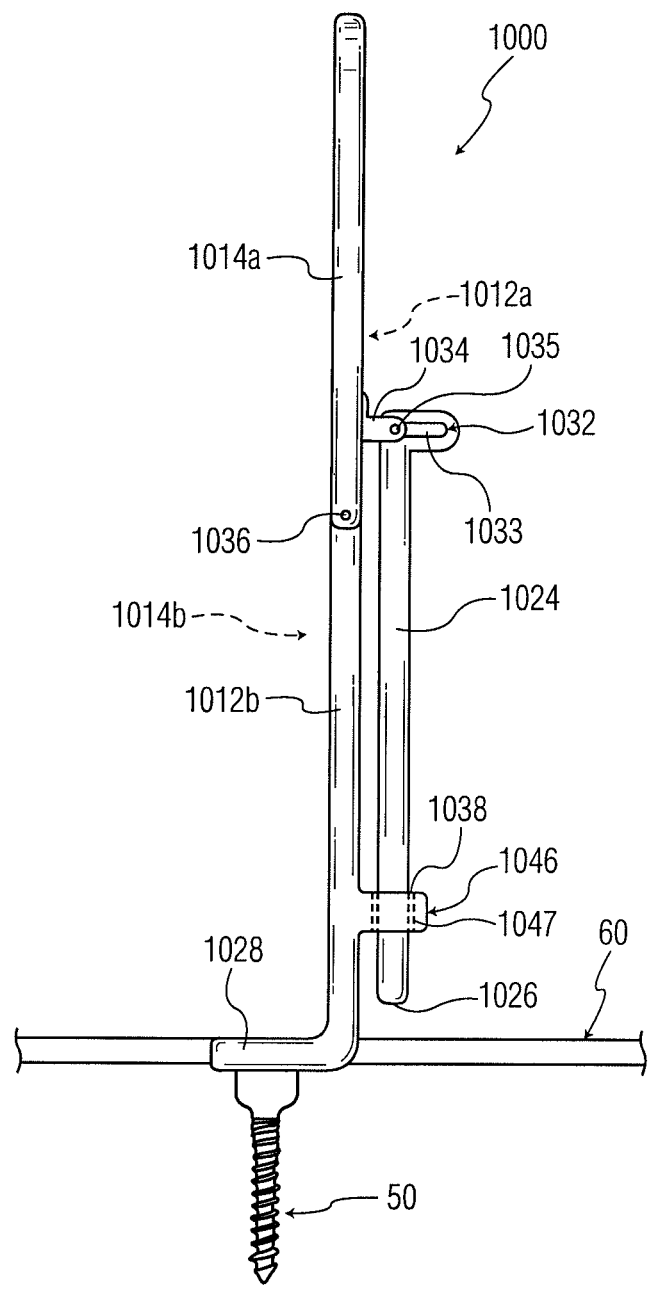
FIGS. 14A-14B are side views showing another embodiment of the rod coercer of the present invention, which includes pivotable upper and lower forceps branches and a rod contacting arm slidably coupled therewith by first and second slidable joints.
Figure 14B:
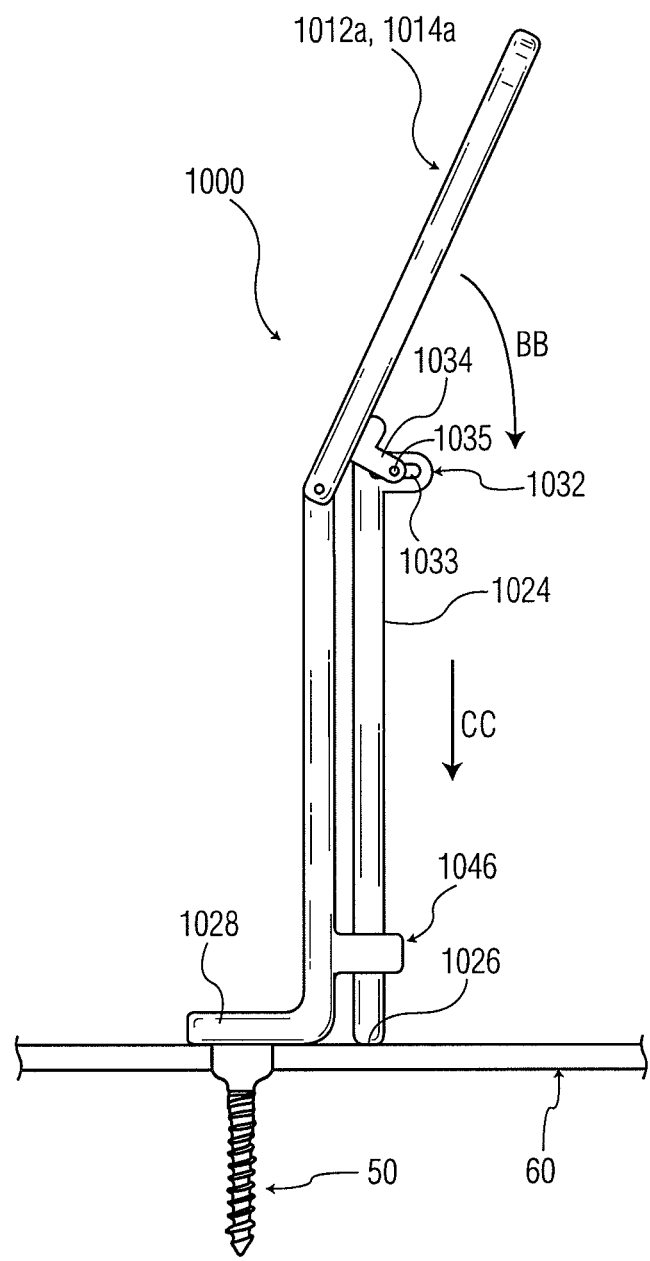

FIGS. 14A-14B are side views showing operation of another embodiment of the rod coercer of the present invention in greater detail, indicated generally at 1000, which includes a rod contacting arm slidably coupled to the coercer by first and second joints. The rod coercer 1000 includes upper handle branches 1012a, 1014a which are pivotally interconnected with lower handle branches 1012b, 1014b by pivotable interconnections 1036. An implant gripping assembly 1028 is provided at the ends of the lower handle branches 1012b, 1014b for gripping the head 52 of the implant 50. First and second joints 1032, 1046 interconnect arm 1024 to the upper and lower branch portions 1014a, 1014b, and allow the arm 1024 to slide. Of course, the joints 1032, 1046 could be attached to the upper and lower branch portions 1012a, 1012b. The arrangement of the upper and lower branch portions is similar to the upper and lower branch portions discussed above in connection with FIGS. 5A-5C.

As shown in FIG. 14A, the joint 1032 includes a bracket 1034 attached to one end of the upper branch portion 1014a. The bracket 1034 includes a pin 1035 which travels along a slot 1032 formed at an upper end of the rod contacting arm 1024, and allows for translation and pivoting of the bracket 1034 and pin 1035 with respect to the slot 1033. The lower end of the rod contacting arm 1024 is linked to the lower branch portion 1014b by the joint 1046. The joint 1046 includes a projection 1046 which is attached to, or formed with, the lower branch portion 1014b, and which includes an aperture 1038 for receiving the contacting arm 1024. The rod contacting arm 1024 translates upwardly and downwardly within the aperture 1038, thereby allowing for slidable coupling of the arm 1024 and the branch 1012b. A curved surface 1026 could be provided at the bottom of the rod contacting arm 1024, which could be shaped to accommodate the rod 60.

As mentioned above, the upper and lower branch portions 1012a, 1014a and 1012b, 1014b are pivotally interconnected by a pivotable interconnection 1036. This allows the upper branch portions 1012a, 1014a to pivot with respect to the lower branch portions 1012b, 1014b, as shown by arrow BB in FIG. 14B. Such movement causes the bracket 1034 and pin 1035 to move along the slot 1033, resulting in the movement of rod contacting arm 1024 downwardly in the general direction indicated by arrow CC, so that the rod contacting arm 1024 contacts the rod 60. This causes the implant 50 and the rod 60 to be drawn together, so as to reduce the rod 60 into the head 52 of the implant 50.

Figure 15C:
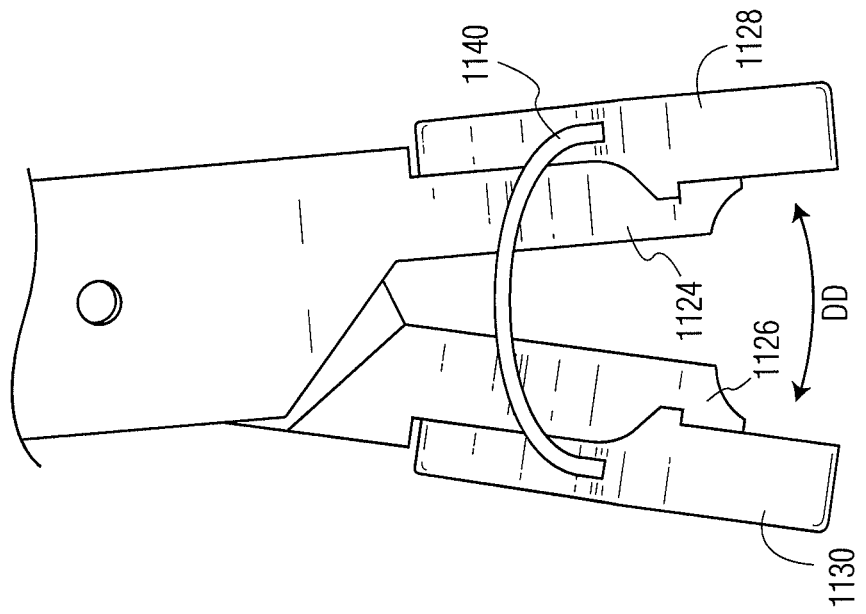
FIGS. 15A-15C are partial perspective and front views showing another embodiment of the rod coercer of the present invention in greater detail, wherein a flexible retainer interconnects the implant gripping arms to maintain the arms in facing relationship.
Figure 15B:
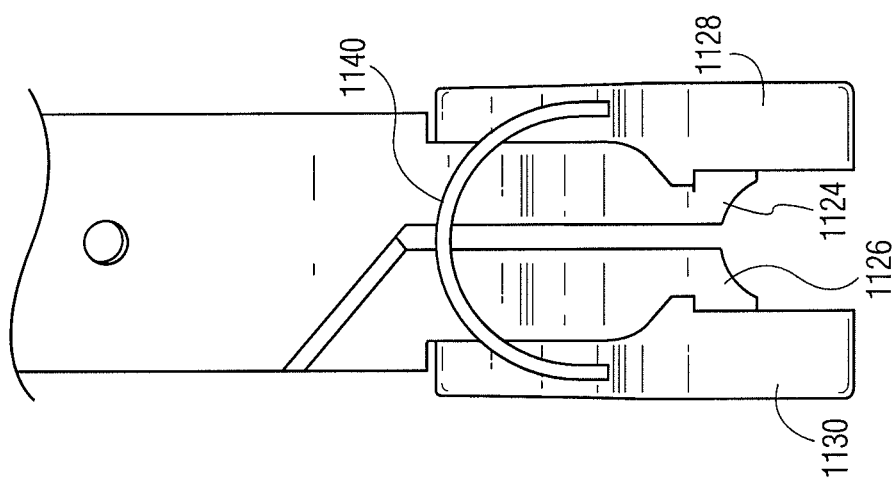
Figure 15A:
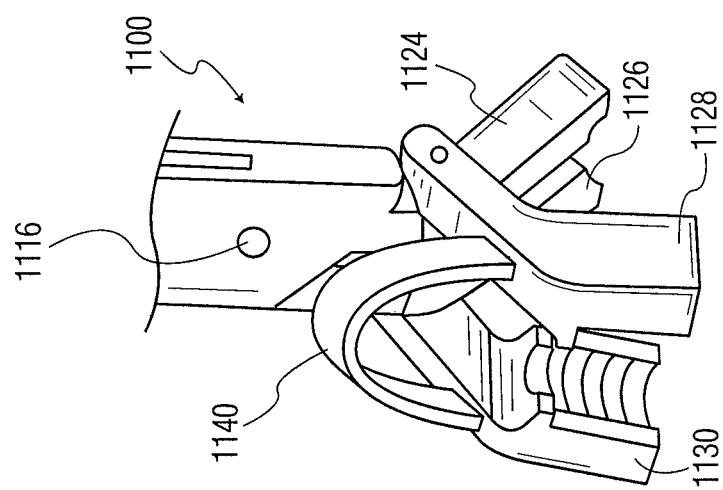

FIGS. 15A-15C are partial perspective and front views showing operation of another embodiment of the rod coercer of the present invention, which is similar in construction to the rod coercer shown in FIG. 9 and is generally indicated at 1100. In this embodiment, a flexible retainer 1140 is provided which interconnects the implant gripping arms 1128, 1130. The retainer 1140 allows the arms 1128, 1130 to be maintained in a facing relationship with each other as they are pivoted about pivot point 1116, as well as when one of the arms 1128, 1130 is moved.

As shown in FIG. 15B, when the arms 1128, 1130 are in a closed arrangement, the retainer 1140 is generally arched. When the arms 1128, 1130 are pivoted in the direction of arrow DD, as shown in FIG. 15C, the retainer 1140 flexes while maintaining the arms 1128, 1130 in facing relationship.

Having thus described the invention in detail, it is to be understood that the foregoing description is not intended to limit the spirit or scope thereof. What is desired to be protected is set forth in the following claims.

What is claimed is:

1. A rod coercer, comprising:
    a handle having at least one rod contacting arm extending therefrom;
    an implant gripping assembly pivotally interconnected with said handle; and
    first and second implant gripping levers pivotally interconnected with said implant gripping assembly and including first and second protrusions biased to engage corresponding recesses of an implant,
    wherein said first and second implant gripping levers are pivotable to selectively retract said first and second protrusions from the recesses of the implant, and said handle is pivotable to urge said rod contacting arm against a rod to reduce the rod into the implant.

2. The rod coercer of claim 1, wherein said first and second implant gripping levers are spring-loaded.

3. The rod coercer of claim 1, wherein said first and second implant gripping levers are L-shaped.

4. The rod coercer of claim 1, wherein the implant gripping assembly includes first and second implant gripping arms.

5. The rod coercer of claim 4, wherein the first and second implant gripping arms each include an aperture through which one of the first and second protrusions extends.

6. The rod coercer of claim 4, wherein said first and second gripping levers are attached to said first and second gripping arms.

7. The rod coercer of claim 1, wherein said first and second gripping levers pivot vertically.

8. The rod coercer of claim 1, wherein said first and second gripping levers pivot horizontally.

9. The rod coercer of claim 1, wherein said first and second protrusions are rounded.

10. The rod coercer of claim 1, wherein said first and second protrusions are angled.

* * * * *